US011420026B2

(12) United States Patent
Zhou et al.

(10) Patent No.: US 11,420,026 B2
(45) Date of Patent: Aug. 23, 2022

(54) EXPANDABLE SHEATH

(71) Applicant: Edwards Lifesciences Corporation, Irvine, CA (US)

(72) Inventors: Pu Zhou, Dove Canyon, CA (US); Erik Bulman, Lake Forest, CA (US); Timothy A. Geiser, Laguna Niguel, CA (US); Michael G. Valdez, Riverside, CA (US); Yidong M. Zhu, Irvine, CA (US); Baigui Bian, Irvine, CA (US); Sonny Tran, Westminster, CA (US); Richard D. White, Costa Mesa, CA (US); Thanh Huy Le, Oceanside, CA (US); Tung T. Le, Irvine, CA (US); Alpana Kiran Gowdar, Irvine, CA (US); Yong Gao, Irvine, CA (US); David Delon Williams, Bountiful, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 383 days.

(21) Appl. No.: 16/550,922

(22) Filed: Aug. 26, 2019

(65) Prior Publication Data
US 2020/0108231 A1 Apr. 9, 2020

Related U.S. Application Data

(63) Continuation of application No. 16/149,671, filed on Oct. 2, 2018, now Pat. No. 10,391,281, which is a (Continued)

(51) Int. Cl.
*A61M 25/06* (2006.01)
*A61F 2/24* (2006.01)
(Continued)

(52) U.S. Cl.
CPC ....... *A61M 25/0662* (2013.01); *A61F 2/2433* (2013.01); *A61F 2/958* (2013.01);
(Continued)

(58) Field of Classification Search
CPC ... A61F 2/962; A61F 2/2427; A61M 25/0054; A61M 25/01
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Julian W Woo
(74) *Attorney, Agent, or Firm* — Meunier Carlin Curfman LLC; Joel B German

(57) ABSTRACT

A delivery sheath includes an outer tubular layer and an initially folded inner tubular layer. When an implant passes therethrough, the outer tubular layer expands and the inner tubular layer unfolds into an expanded lumen diameter. The sheath may also include selectively placed longitudinal support rods that mediate friction between the inner and
(Continued)

outer tubular layers to facilitate easy expansion, thereby reducing the push force needed to advance the implant through the sheath's lumen.

16 Claims, 39 Drawing Sheets

Related U.S. Application Data continuation of application No. 14/880,111, filed on Oct. 9, 2015, now Pat. No. 10,327,896, which is a continuation of application No. 14/880,109, filed on Oct. 9, 2015, now Pat. No. 10,792,471.

(60) Provisional application No. 62/145,968, filed on Apr. 10, 2015.

(51) Int. Cl.
*A61F 2/958* (2013.01)
*A61M 25/00* (2006.01)
*A61F 2/01* (2006.01)

(52) U.S. Cl.
CPC .......... *A61F 2/011* (2020.05); *A61M 25/0023* (2013.01); *A61M 2025/0024* (2013.01)

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,141,364 A * | 2/1979 | Schultze ............... | A61M 16/04 128/207.15 |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,710,181 A | 12/1987 | Fuqua | |
| 4,716,901 A | 1/1988 | Jackson et al. | |
| 4,733,665 A | 3/1988 | Palmaz | |
| 4,738,666 A | 4/1988 | Fuqua | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,921,479 A | 5/1990 | Grayzel | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,104,388 A | 4/1992 | Quackenbush | |
| 5,152,771 A | 10/1992 | Sabbaghian et al. | |
| 5,158,545 A | 10/1992 | Trudell et al. | |
| 5,163,953 A | 11/1992 | Vince | |
| 5,167,628 A | 12/1992 | Boyles | |
| 5,176,659 A | 1/1993 | Mancini | |
| 5,192,297 A | 3/1993 | Hull | |
| 5,201,756 A | 4/1993 | Horzewski et al. | |
| 5,217,468 A | 6/1993 | Clement | |
| 5,226,899 A * | 7/1993 | Lee ....................... | A61L 29/085 604/524 |
| 5,234,425 A | 8/1993 | Fogarty et al. | |
| 5,256,150 A | 10/1993 | Quiachon et al. | |
| 5,266,073 A | 11/1993 | Wall | |
| 5,282,847 A | 2/1994 | Trescony et al. | |
| 5,295,958 A | 3/1994 | Shturman | |
| 5,318,588 A | 6/1994 | Horzewski et al. | |
| 5,332,402 A | 7/1994 | Teitelbaum | |
| 5,360,444 A | 11/1994 | Kusuhara | |
| 5,370,685 A | 12/1994 | Stevens | |
| 5,380,304 A | 1/1995 | Parker | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,514,091 A | 5/1996 | Yoon | |
| 5,514,236 A | 5/1996 | Avellanet et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,599,305 A | 2/1997 | Hermann et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,810,776 A | 9/1998 | Bacich et al. | |
| 5,817,100 A | 10/1998 | Igaki | |
| 5,827,227 A | 10/1998 | DeLago | |
| 5,840,081 A | 11/1998 | Andersen et al. | |
| 5,855,597 A | 1/1999 | Jayaraman | |
| 5,855,601 A | 1/1999 | Bessler et al. | |
| 5,855,602 A | 1/1999 | Angell | |
| 5,895,410 A | 4/1999 | Forber et al. | |
| 5,925,063 A | 7/1999 | Khosravi | |
| 5,957,949 A | 9/1999 | Leonhardt et al. | |
| 5,964,730 A | 10/1999 | Williams et al. | |
| 5,968,068 A | 10/1999 | Dehdashtian et al. | |
| 5,997,508 A | 12/1999 | Lunn et al. | |
| 6,027,525 A | 2/2000 | Suh et al. | |

(56) References Cited

U.S. PATENT DOCUMENTS

| | | |
|---|---|---|
| 6,090,072 A | 7/2000 | Kratoska et al. |
| 6,090,136 A | 7/2000 | McDonald et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,190,357 B1 | 2/2001 | Ferrari et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,312,443 B1 | 11/2001 | Stone |
| 6,338,730 B1 | 1/2002 | Bonutti et al. |
| 6,350,277 B1 | 2/2002 | Kocur |
| 6,352,547 B1 | 3/2002 | Brown et al. |
| 6,358,238 B1 | 3/2002 | Sherry |
| 6,379,372 B1 | 4/2002 | Dehdashtian et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,494,860 B2 | 12/2002 | Rocamora et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,632,236 B2 | 10/2003 | Hogendijk |
| 6,652,578 B2 | 11/2003 | Bailey et al. |
| 6,689,123 B2 | 2/2004 | Pinchasik |
| 6,702,830 B1 | 3/2004 | Demarais et al. |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,814,715 B2 | 11/2004 | Bonutti et al. |
| 6,830,584 B1 | 12/2004 | Seguin |
| 6,878,162 B2 | 4/2005 | Bales et al. |
| 6,893,460 B2 | 5/2005 | Spenser et al. |
| 6,899,727 B2 | 5/2005 | Armstrong et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,144,386 B2 | 12/2006 | Korkor et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,329,268 B2 | 2/2008 | Van Nguyen et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,534,250 B2 | 5/2009 | Schaeffer et al. |
| 7,563,280 B2 | 7/2009 | Anderson et al. |
| 7,585,321 B2 | 9/2009 | Cribier |
| 7,591,832 B2 | 9/2009 | Eversull et al. |
| 7,618,446 B2 | 11/2009 | Andersen et al. |
| 7,618,447 B2 | 11/2009 | Case et al. |
| 7,655,016 B2 | 2/2010 | Demarais et al. |
| 7,655,034 B2 | 2/2010 | Mitchell et al. |
| 7,678,128 B2 | 3/2010 | Boyle et al. |
| 7,699,864 B2 | 4/2010 | Kick et al. |
| 7,713,193 B2 | 5/2010 | Nance et al. |
| 7,722,568 B2 | 5/2010 | Lenker et al. |
| 7,766,820 B2 | 8/2010 | Core |
| 7,780,692 B2 | 8/2010 | Nance et al. |
| 7,785,360 B2 | 8/2010 | Freitag |
| 7,785,366 B2 | 8/2010 | Maurer et al. |
| 7,951,110 B2 | 5/2011 | Bishop et al. |
| 7,959,661 B2 | 6/2011 | Hijlkema et al. |
| 7,959,672 B2 | 6/2011 | Salahieh et al. |
| 7,963,952 B2 | 6/2011 | Wright, Jr. et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,282,664 B2 | 10/2012 | Nance et al. |
| 8,291,570 B2 | 10/2012 | Eidenschink et al. |
| 8,337,518 B2 | 12/2012 | Nance et al. |
| 8,414,645 B2 | 4/2013 | Dwork et al. |
| 8,449,606 B2 | 5/2013 | Eliasen et al. |
| 8,454,685 B2 | 6/2013 | Hariton et al. |
| 8,562,559 B2 | 10/2013 | Bishop et al. |
| 8,562,673 B2 | 10/2013 | Yeung et al. |
| 8,597,277 B2 | 12/2013 | Lenker et al. |
| 8,652,203 B2 | 2/2014 | Quadri et al. |
| 8,728,153 B2 | 5/2014 | Bishop et al. |
| 8,747,463 B2 | 6/2014 | Fogarty et al. |
| 8,790,387 B2 | 7/2014 | Nguyen et al. |
| 8,852,257 B2 | 10/2014 | Liu et al. |
| 8,900,191 B2 | 12/2014 | Lenker et al. |
| 8,900,214 B2 | 12/2014 | Nance et al. |
| 9,078,781 B2 | 7/2015 | Ryan et al. |
| 9,192,751 B2 | 11/2015 | Macaulay et al. |
| 9,241,735 B2 | 1/2016 | Kick et al. |
| 9,301,840 B2 | 4/2016 | Nguyen et al. |
| 9,387,314 B2 | 7/2016 | Bishop et al. |
| 9,440,054 B2 | 9/2016 | Bishop et al. |
| 9,642,704 B2 | 5/2017 | Tuval et al. |
| 9,907,931 B2 | 3/2018 | Birmingham et al. |
| 11,154,690 B2 * | 10/2021 | Avneri ............ A61M 25/0133 |
| 2001/0021872 A1 | 9/2001 | Bailey et al. |
| 2002/0026094 A1 | 2/2002 | Roth |
| 2002/0032459 A1 | 3/2002 | Horzewski et al. |
| 2002/0032481 A1 | 3/2002 | Gabbay |
| 2002/0123793 A1 | 9/2002 | Schaldach et al. |
| 2002/0138135 A1 | 9/2002 | Duerig et al. |
| 2002/0173842 A1 | 11/2002 | Buchanan |
| 2003/0004537 A1 | 1/2003 | Boyle et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0087968 A1 | 5/2004 | Core |
| 2004/0122415 A1 | 6/2004 | Johnson |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0080430 A1 | 4/2005 | Wright et al. |
| 2005/0080474 A1 | 4/2005 | Andreas et al. |
| 2005/0085842 A1 | 4/2005 | Eversull et al. |
| 2005/0096736 A1 | 5/2005 | Osse et al. |
| 2005/0124937 A1 | 6/2005 | Kick et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0222576 A1 | 10/2005 | Kick et al. |
| 2005/0234546 A1 | 10/2005 | Nugent et al. |
| 2006/0004469 A1 | 1/2006 | Sokel |
| 2006/0020321 A1 | 1/2006 | Parker |
| 2006/0025857 A1 | 2/2006 | Bergheim et al. |
| 2006/0058872 A1 | 3/2006 | Salahieh et al. |
| 2006/0135962 A1 | 6/2006 | Kick et al. |
| 2006/0135981 A1 | 6/2006 | Lenker et al. |
| 2006/0149350 A1 | 7/2006 | Patel et al. |
| 2006/0183383 A1 | 8/2006 | Asmus et al. |
| 2006/0217755 A1 | 9/2006 | Eversull et al. |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |

(56) References Cited

U.S. PATENT DOCUMENTS

| | | |
|---|---|---|
| 2007/0010877 A1 | 1/2007 | Salahieh et al. |
| 2007/0021768 A1 | 1/2007 | Nance et al. |
| 2007/0074805 A1 | 4/2007 | Leeflang et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0004571 A1 | 1/2008 | Voss |
| 2008/0114331 A1 | 5/2008 | Holman et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0200943 A1 | 8/2008 | Barker et al. |
| 2008/0243081 A1 | 10/2008 | Nance et al. |
| 2008/0255447 A1 | 10/2008 | Bourang et al. |
| 2008/0275537 A1 | 11/2008 | Limon |
| 2008/0294230 A1 | 11/2008 | Parker |
| 2008/0300544 A1 | 12/2008 | Palm |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287182 A1 | 11/2009 | Bishop et al. |
| 2009/0299452 A1 | 12/2009 | Eidenschink et al. |
| 2009/0319037 A1 | 12/2009 | Rowe et al. |
| 2010/0049313 A1 | 2/2010 | Mon et al. |
| 2010/0094392 A1 | 4/2010 | Nguyen et al. |
| 2010/0168844 A1 | 7/2010 | Toomes et al. |
| 2010/0198160 A1 | 8/2010 | Voss |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0112567 A1 | 5/2011 | Lenker et al. |
| 2011/0251681 A1 | 10/2011 | Shipley et al. |
| 2011/0319991 A1 | 12/2011 | Hariton et al. |
| 2012/0083877 A1 | 4/2012 | Nguyen et al. |
| 2012/0123529 A1 | 5/2012 | Levi et al. |
| 2012/0158033 A1 | 6/2012 | Deal et al. |
| 2012/0259409 A1 | 10/2012 | Nguyen et al. |
| 2013/0023985 A1 | 1/2013 | Khairkhahan et al. |
| 2013/0030369 A1 | 1/2013 | Root et al. |
| 2013/0083877 A1 | 4/2013 | Gorokhov |
| 2013/0090624 A1 | 4/2013 | Munsinger |
| 2013/0131718 A1 | 5/2013 | Jenson et al. |
| 2013/0190857 A1 | 7/2013 | Mitra et al. |
| 2013/0274873 A1 | 10/2013 | Delaloye et al. |
| 2013/0281787 A1 | 10/2013 | Avneri et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2013/0338677 A1 | 12/2013 | Schwitzer et al. |
| 2014/0121329 A1 | 5/2014 | Araki et al. |
| 2014/0121629 A1 | 5/2014 | Macaulay et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0236122 A1 | 8/2014 | Anderson et al. |
| 2014/0236123 A1 | 8/2014 | Birmingham et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2014/0379067 A1 | 12/2014 | Nguyen et al. |
| 2015/0073545 A1 | 3/2015 | Braido |
| 2015/0073546 A1 | 3/2015 | Braido |
| 2016/0074067 A1 | 3/2016 | Furnish et al. |
| 2018/0199960 A1 | 7/2018 | Anderson et al. |
| 2018/0229000 A1 | 8/2018 | Anderson et al. |
| 2019/0030298 A1 | 1/2019 | Zhou et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0177177 A2 | 4/1986 |
| EP | 0249456 A2 | 12/1987 |
| EP | 0385920 A2 | 9/1990 |
| EP | 3597967 A1 | 5/1994 |
| EP | 0592410 B1 | 10/1995 |
| EP | 0696447 A2 | 2/1996 |
| EP | 0839549 A1 | 5/1998 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| FR | 2788217 A1 | 7/2000 |
| FR | 2815844 A1 | 5/2002 |
| GB | 2056023 A | 3/1981 |
| JP | 2004500171 A | 1/2004 |
| JP | 2006116249 A | 5/2006 |
| SU | 1271508 A1 | 11/1986 |
| WO | 9117720 A1 | 11/1991 |
| WO | 9217118 A1 | 10/1992 |
| WO | 9219312 A1 | 11/1992 |
| WO | 9301768 A1 | 2/1993 |
| WO | 9307812 A1 | 4/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 33002181 A2 | 1/2003 |
| WO | 03047468 A1 | 6/2003 |
| WO | 2020403733 A2 | 1/2004 |
| WO | 20204002562 A2 | 1/2004 |
| WO | 20204037333 A1 | 5/2004 |
| WO | 20205018728 A2 | 3/2005 |
| WO | 20205034812 A1 | 4/2005 |
| WO | 20205084595 A1 | 9/2005 |
| WO | 20206014233 A2 | 2/2006 |
| WO | 20206032051 A2 | 3/2006 |
| WO | 20206034008 A2 | 3/2006 |
| WO | 20206111391 A1 | 10/2006 |
| WO | 20206127089 A1 | 11/2006 |
| WO | 20206138173 A2 | 12/2006 |
| WO | 20207035471 A2 | 3/2007 |
| WO | 20205102015 A3 | 4/2007 |
| WO | 20207047488 A2 | 4/2007 |
| WO | 20207067942 A1 | 6/2007 |
| WO | 20207097983 A2 | 8/2007 |

(56) References Cited

FOREIGN PATENT DOCUMENTS

| WO | 20208002915 | A2 | 1/2008 |
|---|---|---|---|
| WO | 20208005405 | A2 | 1/2008 |
| WO | 20208015257 | A2 | 2/2008 |
| WO | 20208035337 | A2 | 3/2008 |
| WO | 20208042311 | A1 | 4/2008 |
| WO | 20208091515 | A2 | 7/2008 |
| WO | 20208147964 | A1 | 12/2008 |
| WO | 20208150529 | A1 | 12/2008 |
| WO | 20209033469 | A1 | 3/2009 |
| WO | 202010121076 | A2 | 10/2010 |
| WO | 2011133513 | A2 | 10/2011 |
| WO | 2014140093 | A1 | 9/2014 |
| WO | 202014182959 | A2 | 11/2014 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187 1986.

English translation of Second Office Action issued in Chinese Application No. 2019108734650, dated Jan. 13, 2022.

* cited by examiner

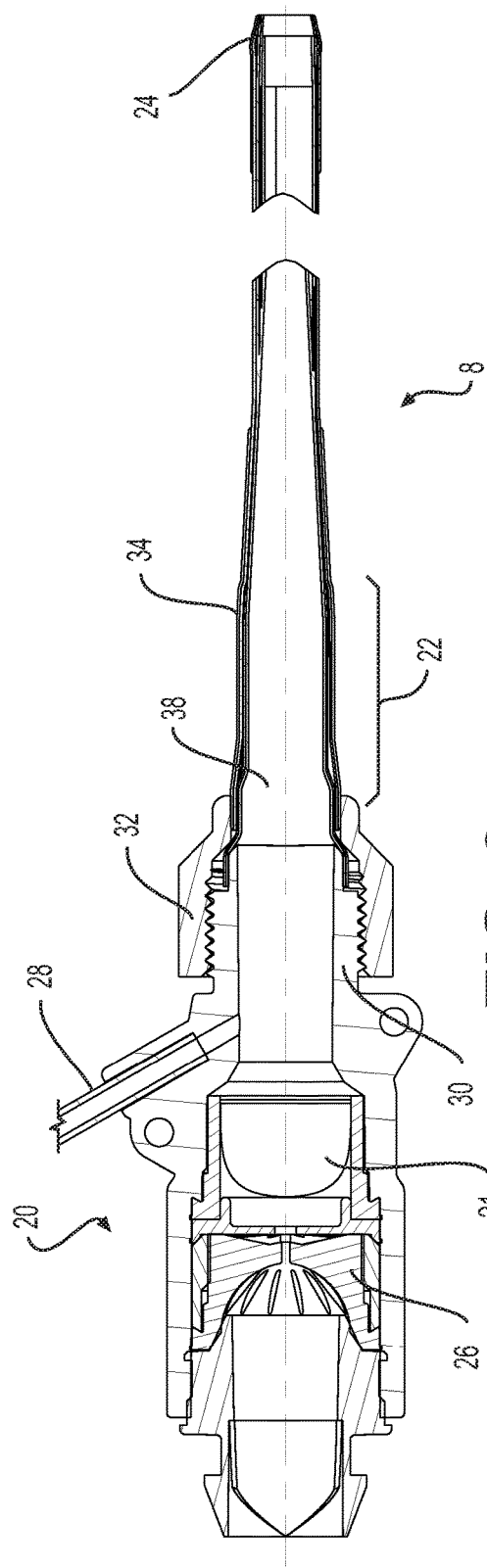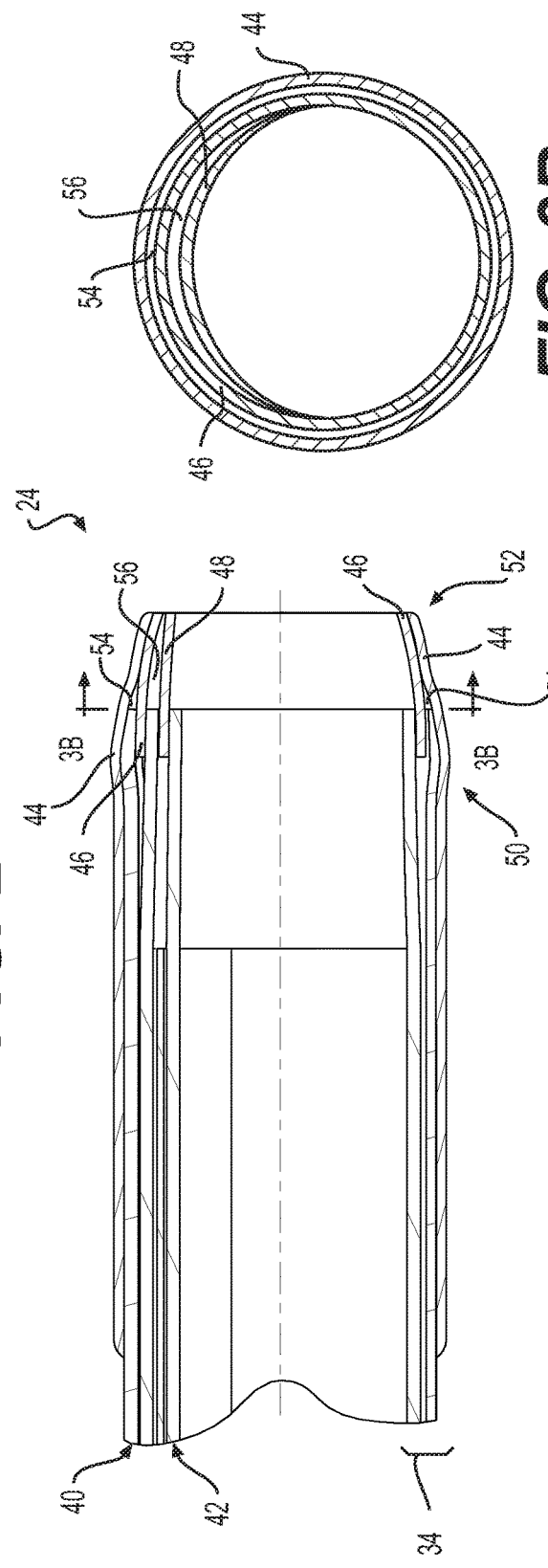

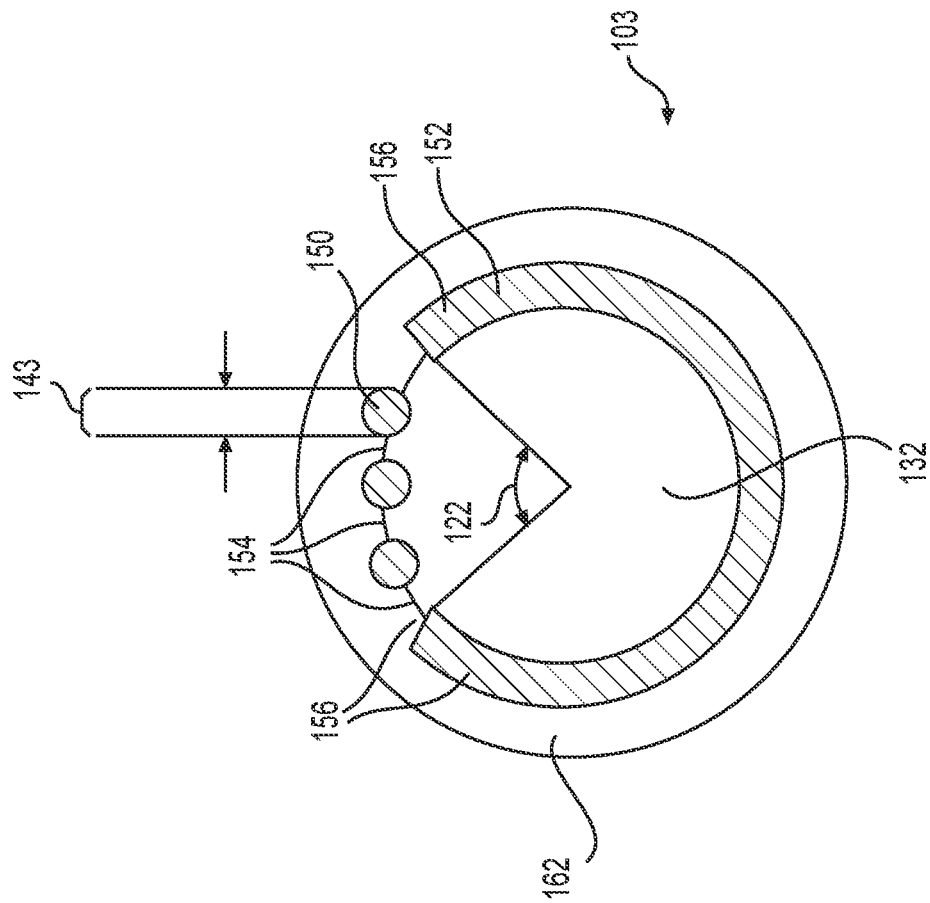
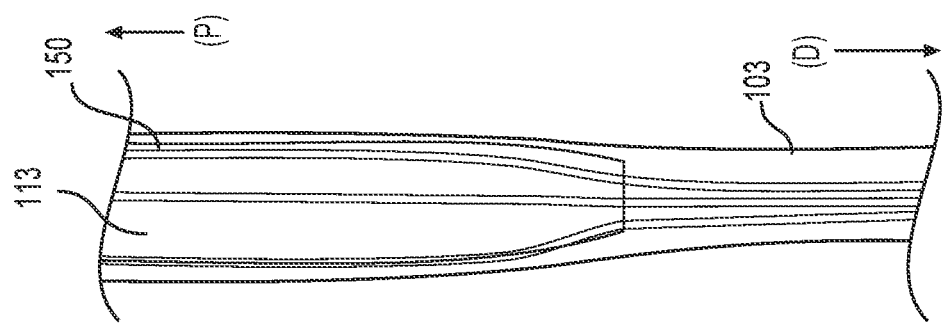

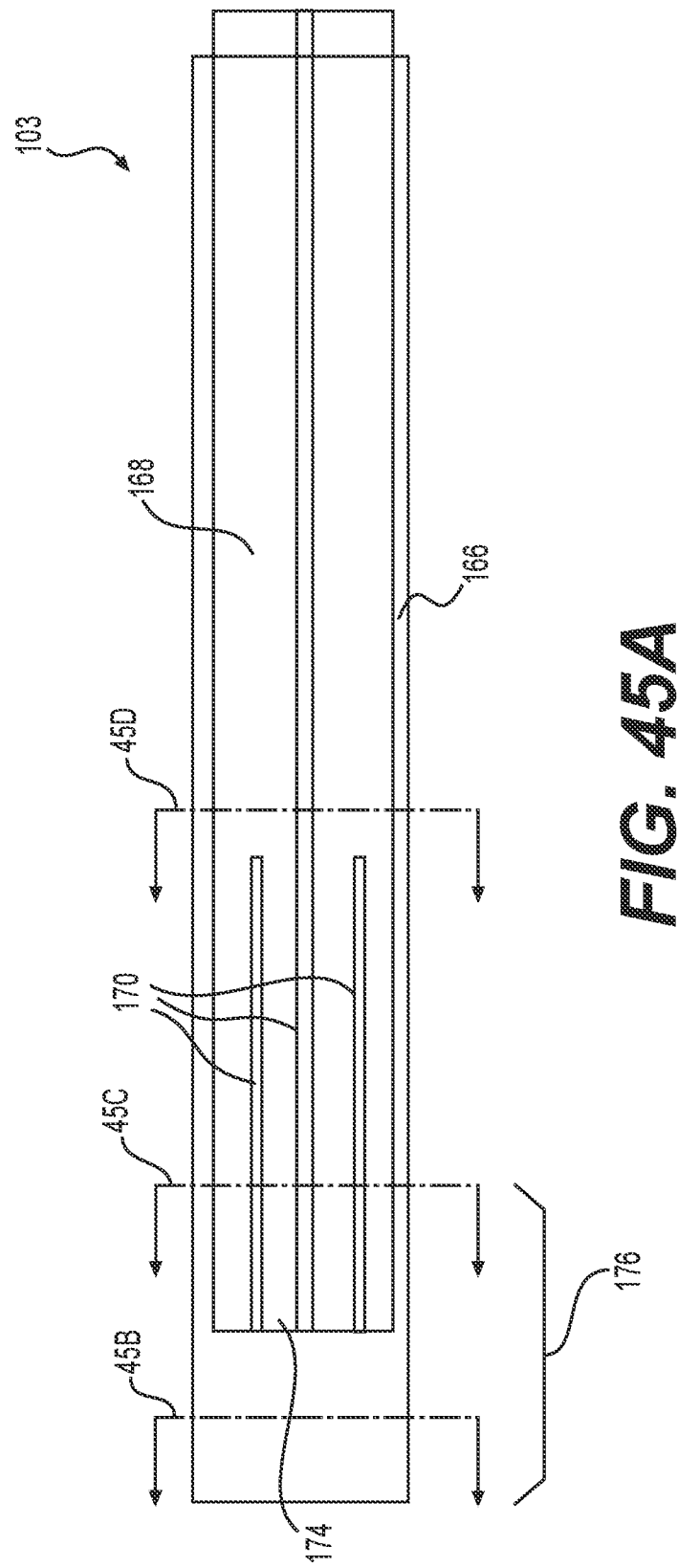

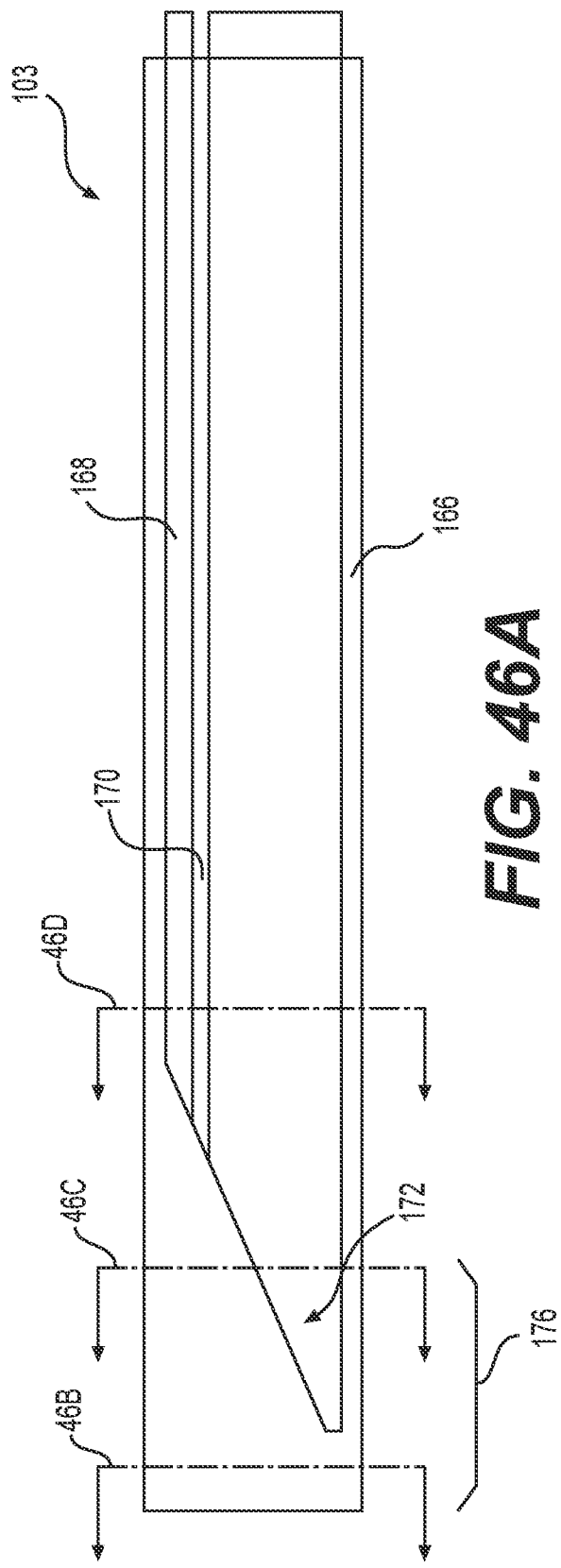

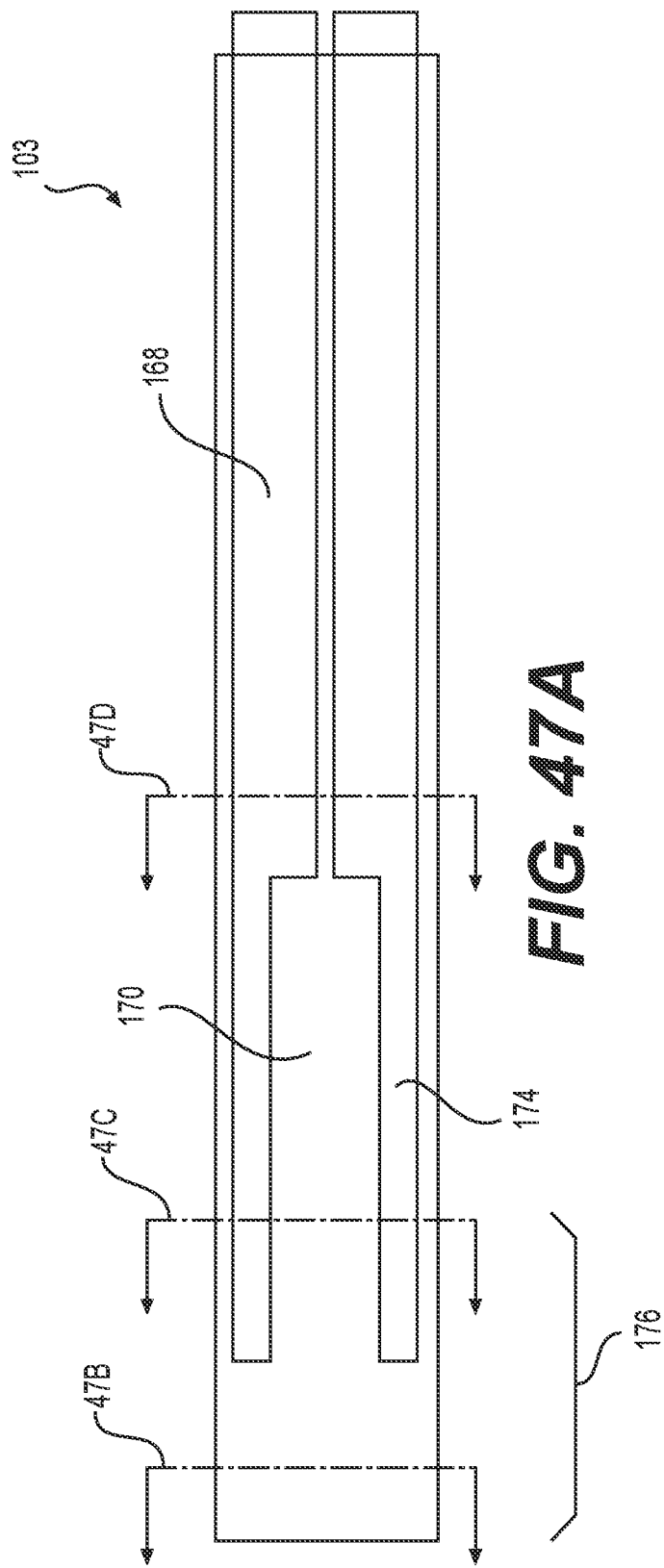

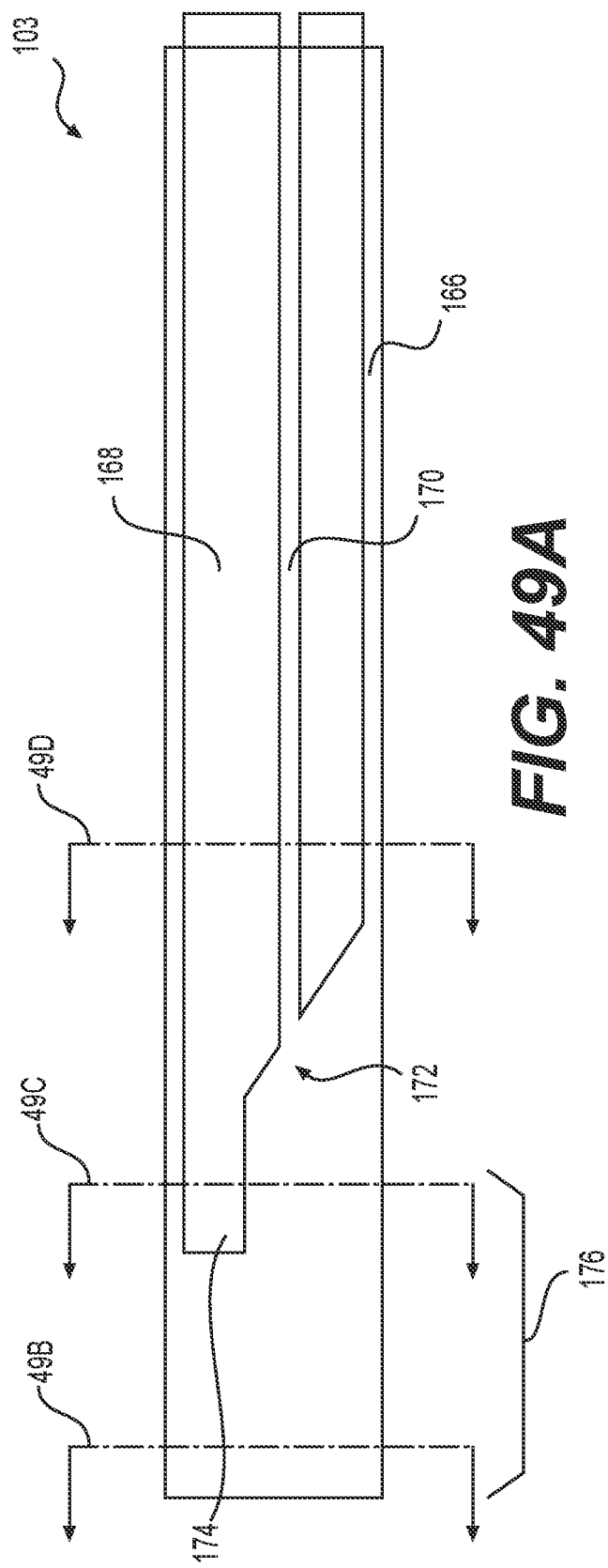

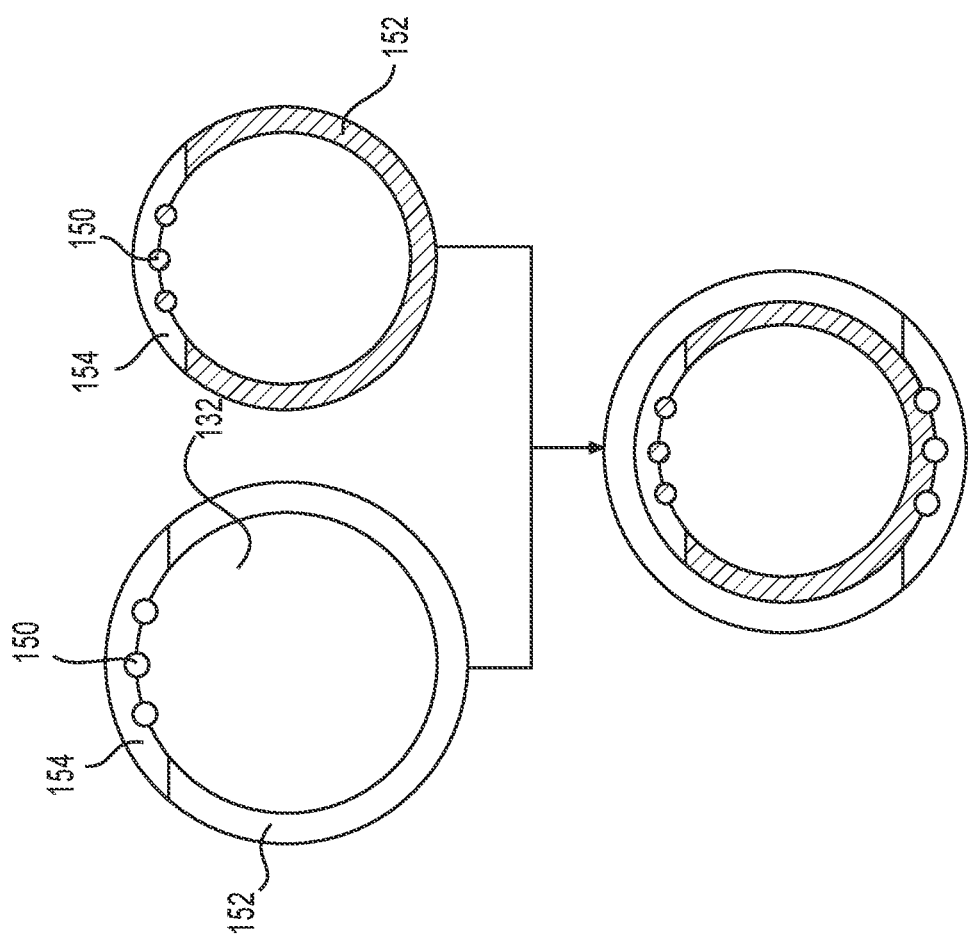

EXPANDABLE SHEATH

RELATED APPLICATIONS

This application is a continuation of U.S. application Ser. No. 16/149,671, filed Oct. 2, 2018, entitled EXPANDABLE SHEATH. U.S. application Ser. No. 16/149,671 is a continuation of U.S. application Ser. No. 14/880,109, filed Oct. 9, 2015, and entitled EXPANDABLE SHEATH, which claims the benefit of U.S. Provisional Patent Application Ser. No. 62/145,968 filed on Apr. 10, 2015 and entitled EXPANDABLE DELIVERY SHEATH. U.S. application Ser. No. 16/149,671 is also a continuation of U.S. application Ser. No. 14/880,111, filed Oct. 9, 2015, now U.S. Pat. No. 10,327,896, and entitled EXPANDABLE SHEATH WITH ELASTOMERIC CROSS SECTIONAL PORTIONS, which claims the benefit of U.S. Provisional Patent Application Ser. No. 62/145,968, filed Apr. 10, 2015 and entitled EXPANDABLE DELIVERY SHEATH. All of the aforementioned applications are hereby incorporated by reference herein in their entireties and for all purposes.

FIELD

The present application concerns embodiments of a sheath for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

U.S. Pat. No. 8,790,387, which is entitled EXPANDABLE SHEATH FOR INTRODUCING AN ENDOVASCULAR DELIVERY DEVICE INTO A BODY and is incorporated herein by reference, discloses a sheath with a split outer polymeric tubular layer and an inner polymeric layer, for example in FIGS. 27A and 28. A portion of the inner polymeric layer extends through a gap created by the cut and can be compressed between the portions of the outer polymeric tubular layer. Upon expansion of the sheath, portions of the outer polymeric tubular layer have separated from one another, and the inner polymeric layer is expanded to a substantially cylindrical tube. Advantageously, the sheath disclosed in the '387 patent can temporarily expand for passage of implantable devices and then return to its starting diameter.

Despite the disclosure of the '387 patent, there remains a need for further improvements in introducer sheaths for endovascular systems used for implanting valves and other prosthetic devices.

SUMMARY

The needs above and other advantages are provided by an expandable introducer sheath for a delivery of an implant mounted on a catheter. The sheath includes an elastic outer tubular layer and an inner tubular layer having a thick wall portion integrally connected to a thin wall portion. The inner tubular layer can have a compressed condition/folded configuration wherein the thin wall portion folds onto an outer surface of the thick wall portion under urging of the elastic outer tubular layer. When the implant passes therethrough, the outer tubular layer stretches and the inner tubular layer at least partially unfolds into an expanded lumen diameter to accommodate the diameter of the implant. Once the implant passes, the outer tubular layer again urges the inner tubular layer into the folded configuration with the sheath reassuming its smaller profile. In addition to a reduced initial profile size, the integral construction of the inner tubular layer guards against the leaks and snags of prior art split-tube and uniform thickness liner combinations. The sheath may also include selectively placed longitudinal rods that mediate friction between the inner and outer tubular layers to facilitate easy expansion and collapse, thereby reducing the push force needed to advance the oversized implant through the sheath's lumen.

Embodiments include a sheath for delivery of an implant mounted on a catheter. The sheath may include an elastic outer tubular layer and an inner tubular layer. The outer tubular layer defines an initial elastic lumen extending axially therethrough and having an initial diameter. The inner tubular layer has a thick wall portion integrally connected to a thin wall portion—such as by co-extrusion during manufacture. The thick wall portion has a C-shaped cross section with a first longitudinally extending end and a second longitudinally extending end. The thin wall portion extends between the first and second longitudinally extending ends to define an expanded lumen extending axially through the inner tubular layer. The expanded lumen has an expanded diameter larger than the initial diameter of the initial elastic lumen. The inner tubular layer, in a compressed condition, extends through the initial elastic lumen of the elastic outer tubular layer with the elastic outer tubular layer urging the first longitudinally extending end under the second longitudinally extending end of the inner tubular layer. The inner tubular layer in a locally expanded condition has the first and second longitudinally extending ends radially expanded apart, against the urging of the elastic outer tubular layer by passage of the implant, into a non-overlapping condition with the thin wall portion extending therebetween to form the expanded lumen. The inner tubular layer is configured to be urged by the outer elastic tubular layer into the compressed condition after passage of the implant through the expanded lumen.

In another aspect, the outer surface of the inner tubular layer and/or the inner surface of the outer tubular layer can have a lubricious coating configured to allow free relative sliding of the outer elastic layer and inner tubular layer. A longitudinally extending portion or strip of the outer surface of the inner tubular layer can be adhered to a corresponding longitudinally extending portion of the inner surface of the outer tubular layer to provide some restriction on rotation between the inner and outer layer.

In another embodiment, the tubular layers may include a plurality of longitudinal rods coupled to their surfaces. For example, the inner surface of the outer tubular layer may include rods extending into the initial elastic lumen. The rods are configured to provide a bearing surface to facilitate relative movement of the layers when moving from the locally expanded condition to the compressed condition (and back). Longitudinal rods embedded within the elastic outer tubular layer can also protrude from both an inner and outer surface of the elastic outer tubular layer.

The longitudinal rods may be circumferentially spaced about the inner surface of the outer tubular layer. The inner tubular layer may also include contact-area reducing rods coupled to its inner surface.

In another aspect, the sheath can include a radiopaque tubular layer extending around a longitudinal portion of the elastic outer tubular layer. In some embodiments, the outer tubular layer is comprised of a transparent material In some embodiments, a heat-shrink tube can be applied around the elastic outer tubular layer at a distal end of the elastic outer tubular layer.

In some embodiments, a distal portion of the elastic outer tubular layer and inner tubular layer are adhered to each other. For example, a distal portion of the elastic outer tubular layer can be adhered to an expanded outer surface of the inner tubular layer. The distal portion of the elastic outer tubular layer and inner tubular layer can be reflowed onto each other into a sealed configuration. In some implementations, a distal portion of the sheath has a flared shape. The flared shape can be folded into an overlapping arrangement.

A method of using the expandable introducer sheath can include inserting the sheath, at least partially, into the blood vessel of the patient. An implant is advanced through the inner tubular layer of the sheath. The inner tubular layer transitions from a compressed condition to a locally expanded condition using the outwardly directed radial force of the implant. After passage of the implant, the locally expanded inner tubular layer is contracted at least partially back to the compressed condition by the inwardly directed radial force of the outer elastic tubular layer. During the local expansion of the inner tubular layer, the first and second longitudinally extending ends move towards and then away from each other. During contraction of the locally expanded inner tubular layer, the first and second longitudinally extending ends move toward and then away from each other to return, at least partially, to the compressed condition.

Disclosed herein is an expandable introducer sheath for passage of implant delivery catheters, such as catheters for delivery of prosthetic heart valves. The expandable sheath can minimize trauma to the vessel by allowing for temporary expansion of a portion of the expandable sheath to accommodate the delivery catheter, followed by a return to the original diameter once the implant passes through. Generally, disclosed herein, are various embodiments balancing the amounts, shapes and positions of various stiff and elastic structures in the sheath to selectively program the expandability and buckling stiffness of the sheath. The expandable sheath can include, for example, an expandable tubular layer that includes alternating stiff and elastic wall portions of a single radial thickness. The combination of stiff and elastic wall portions allow for torque and push strength to advance the expandable sheath while at the same time accommodating temporary expansion. The expandable sheath can also be reinforced with a tubular layer of braided fibers or a stent structure for additional strength. Other embodiments include selective use of slots or gaps at the distal end of a stiff wall portion to enhance expandability and distribute strain.

A sheath of one embodiment includes at least one stiff wall portion and elastic wall portion arranged into an expandable tubular layer. The stiff wall portion has a stiff wall radial thickness and extends generally parallel to and partially around an elongate axis of the sheath and defines at least two edges. The two edges extend generally axially and between an inner surface and outer surface of the stiff wall portion. The stiff wall portion has an elastic wall radial thickness equal to the stiff wall radial thickness and extends generally parallel to and partially around the elongate axis. The elastic wall portion extends between the edges of the stiff wall portion so as to define the expandable tubular layer with a consistent radial thickness at any one cross-section. The expandable tubular layer has a starting profile smaller than the implant and defines a lumen. The expandable layer is configured to temporarily expand at least at the elastic wall portion to allow passage of the implant through the lumen. The expandable layer then returns to its original shape to approximate the starting profile after passage of the implant through the lumen.

In another aspect, the at least one stiff wall portion includes a plurality of stiff wall portions. And, the at least one elastic wall portion includes a plurality of elastic wall portions. The stiff and elastic wall portions can alternate circumferentially around the elongate axis. Also, the sheath can include an elastic outer tubular layer extending around the expandable tubular layer. The sheath can also include an intermediate tubular layer comprising a plurality of braided fibers extending between the expandable tubular layer and the outer tubular layer. The braided tubular fibers can also form an expandable mesh, wherein the elastic outer tubular layer is laminated onto the intermediate tubular layer. The sheath can also include a low friction tubular layer coating the inner surface of the expandable tubular layer. The fibers can extend generally perpendicular to each other to form the expandable mesh.

In another aspect, the two edges of each of the stiff wall portions can extend parallel to the elongate axis. And, the stiff wall portions can be arc segments of the expandable tubular layer.

In another embodiment, the sheath includes a stiff wall portion and an elastic wall portion defining an expandable tubular layer. The stiff wall portion extends generally parallel to and partially around an elongate axis of the sheath and defines at least two edges. The two edges extend generally axially and between an inner and outer surfaces of the stiff wall portion. The elastic wall portion extends generally parallel to and partially around the elongate axis. The elastic wall portion extends between the edges of the stiff wall portion so as to define the expandable tubular layer. The expandable tubular layer has a starting profile smaller than the implant and defines a lumen. And, the expandable tubular layer is configured to temporarily expand at least at the elastic wall portion to allow passage of the implant through the lumen and then return to approximate the starting profile after passage of the implant through the lumen. The elastic wall portion (or portions) can comprise 45 degrees to 90 degrees of an axial cross-section of the expandable tubular layer.

The sheath can also include one or more elongate rods coupled to an inner surface of the elastic wall portion and extending generally parallel to the elongate axis. The stiff wall portion and the elongate rods can have a lubricious inner surface configured to facilitate passage of the implant. The elastic wall portion can also be part of an outer elastic tubular layer and the stiff wall portion can be embedded in the outer elastic tubular layer. The lumen of the expandable tubular layer can be larger where it is defined by the elastic wall portion than where it is defined by the stiff wall portion.

In another aspect, a plurality of elongate rods are coupled to an inner surface of the elastic wall portion and the inner surface of the stiff wall portion. The elongate rods extend generally parallel to the elongate axis and inward into the lumen. The elongate rods can also be spaced circumferentially apart around the lumen of the expandable tubular layer.

In another embodiment, the sheath includes an elastic tubular layer and at least one stiff wall embedded in the elastic tubular layer. A proximal portion of the stiff wall defines at least one first longitudinally extending gap and a distal portion defines at least one second longitudinally extending gap. A cumulative circumferential size of the at least one first longitudinally extending gap is smaller than a cumulative circumferential size of the at least one second longitudinally extending gap. The sheath has a starting profile smaller than the implant and defines a lumen. The sheath is configured to temporarily expand at the at least one first longitudinal gap and the at least one second longitudinal gap to allow passage of the implant through the lumen and then to return to approximate the starting profile after passage of the implant through the lumen.

The second longitudinally extending gap can extent from a distal end of the first longitudinally extending gap.

Also, the sheath can include twice as many second gaps as first gaps. A distal end of each of the first longitudinally extending gaps can extend to a proximal end of a corresponding one of the second longitudinally extending gaps. In another aspect, the sheath can include six second longitudinally extending gaps.

The at least one second longitudinally extending gap can include at least a portion having a progressively, distally increasing cumulative circumferential size.

In another aspect, the sheath includes a plurality of second longitudinal gaps extending linearly and defining a plurality of stiff wall fingers.

DESCRIPTION OF DRAWINGS

FIG. 2 is a cross sectional view of a sheath and a hub.

FIG. 3A is a magnified view of distal tip of the sheath.

FIG. 3B is a cross sectional view of the distal tip of the sheath, taken along line 3B-3B of FIG. 3A.

FIG. 43A is an enlarged view of a sheath of another embodiment with a capsule passing therethrough;

FIG. 43B is a cross sectional view of the sheath of FIG. 43A;

FIG. 45A is a schematic of another implementation of a delivery sheath with increasing elasticity approaching the distal end region;

FIG. 46A is a schematic of another implementation of a delivery sheath with increasing elasticity approaching the distal end region;

FIG. 47A is a schematic of another implementation of a delivery sheath with increasing elasticity approaching the distal end region;

FIG. 49A is a schematic of another implementation of a delivery sheath with increasing elasticity approaching the distal end region.

FIG. 50 is a schematic of assembly of two sheaths into a combination sheath of another embodiment of the present invention;

DETAILED DESCRIPTION

Figure 1:
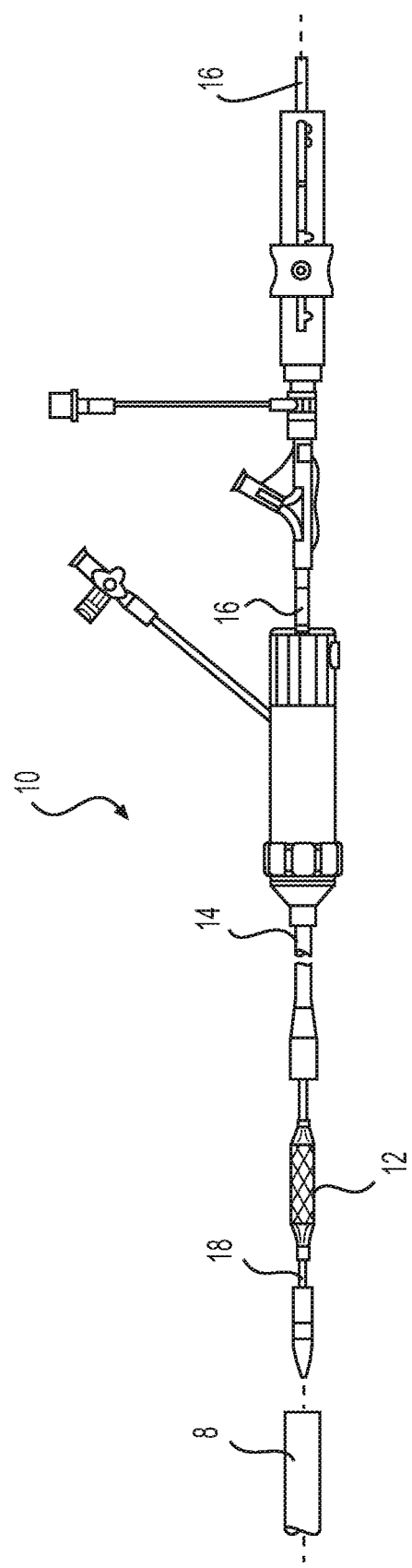
FIG. 1 is an elevation view of an expandable sheath along with an endovascular delivery apparatus for implanting a prosthetic implant.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed embodiments of an expandable sheath can minimize trauma to the vessel by allowing for temporary expansion of a portion of the introducer sheath to accommodate the delivery system, followed by a return to the original diameter once the device passes through. The expandable sheath can include, for example, an integrally formed inner tubular layer with thick and thin wall portions, wherein the thin wall portion can expand to an expanded lumen for passage of an implant and then fold back onto itself under biasing of an outer elastic tubular layer after departure of the implant. In another aspect, the expandable sheath can include one or more longitudinally oriented stiffening elements (such as rods) that are coupled to the elastic outer layer to provide stiffness for the expandable sheath. Some embodiments can comprise a sheath with a smaller profile than the profiles of prior art introducer sheaths. Furthermore, present embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can avoid the need for multiple insertions for the dilation of the vessel.

Disclosed herein is an expandable introducer sheath for passage of implant delivery catheters, such as catheters for delivery of prosthetic heart valves. The expandable sheath can minimize trauma to the vessel by allowing for temporary expansion of a portion of the expandable sheath to accommodate the delivery catheter, followed by a return to the original diameter once the implant passes through. Generally, disclosed herein, are various embodiments balancing the amounts, shapes and positions of various stiff and elastic structures in the sheath to selectively program the expandability and buckling stiffness of the sheath. The expandable sheath can include, for example, an expandable tubular layer that includes alternating stiff and elastic wall portions of a single radial thickness. The combination of stiff and elastic wall portions allow for torque and push strength to advance the expandable sheath while at the same time accommodating temporary expansion. The expandable sheath can also be reinforced with a tubular layer of braided fibers or a stent structure for additional strength. Other embodiments include selective use of slots or gaps at the distal end of a stiff wall portion to enhance expandability and distribute strain.

Disclosed herein are elongate delivery sheaths that are particularly suitable for delivery of implants in the form of implantable heart valves, such as balloon-expandable implantable heart valves. Balloon-expandable implantable heart valves are well-known and will not be described in detail here. An example of such an implantable heart valve is described in U.S. Pat. No. 5,411,552, and also in U.S. Patent Application Publication No. 2012/0123529, both of which are hereby incorporated by reference. The elongate delivery sheaths disclosed herein may also be used to deliver other types of implantable devices, such as self-expanding implantable heart valves, stents or filters. The term "implantable" as used herein is broadly defined to mean anything— prosthetic or not—that is delivered to a site within a body. A diagnostic device, for example, may be an implantable.

The term "tube" or "tubular" as used herein is not meant to limit shapes to circular cross-sections. Instead, tube or tubular can refer to any elongate structure with a closed-cross section and lumen extending axially therethrough. A tube can also have some selectively located slits or openings therein—although it still will provide enough of a closed structure to contain other components within its lumen(s).

FIG. 1 illustrates an exemplary sheath 8 in use with a representative delivery apparatus 10, for delivering an implant 12, or other type of implantable, to a patient. The apparatus 10 can include a steerable guide catheter 14 (also referred to as a flex catheter) and a balloon catheter 16 extending through the guide catheter 14. The guide catheter 14 and the balloon catheter 16 in the illustrated embodiment are adapted to slide longitudinally relative to each other to facilitate delivery and positioning of the implant 12 at an implantation site in a patient's body, as described in detail below. The sheath 8 is an elongate, expandable tube that can include a hemostasis valve at the opposite, proximal end of the sheath to stop blood leakage.

Generally, during use a distal end of the sheath 8 is passed through the skin of the patient and inserted into a vessel, such as the trans-femoral vessel. The delivery apparatus 10 can be inserted into the sheath 8 through the hemostasis valve, and the implant 12 can then be delivered and implanted within the patient.

As shown in FIG. 2, the sheath 8 includes a hub 20, a flared proximal end 22 and a distal tip 24. The hub 20 is constructed of a rigid cylindrical structure defining a hub lumen 21 and houses a hemostasis valve 26 and may define a side port 28 and have a threaded distal end 30. The flared proximal end 22 of the sheath 8 includes a threaded female connector 32 mounted on a tubular wall structure 34. The distal tip 24 of the sheath 8 is mounted over a distal end of the tubular wall structure 34, as shown in FIG. 3. The tubular wall structure 34 defines a central lumen 38.

The hub 20 is attached to the flared proximal end 22 by twisting the threaded distal male end 30 into correspondingly threaded female connector 32. This places the hub lumen 21 in communication with the central lumen 38 of the tubular wall structure 34. The hemostasis valve 26 mediates access by the delivery apparatus 10 to the hub lumen 21 and central lumen 38 and ultimate deployment of the implant 12 in a pressurized (blood filled) environment. Side port 28 provides an additional access for application of saline or other fluids.

The distal tip 24, meanwhile, provides some restraint to the otherwise radially expandable tubular wall structure 34. The distal tip 24 also helps with advancement over an introducer by providing a tapered advancement surface. Further the distal tip 24 improves the stiffness of the sheath 8 at its distal tip to guard against buckling or collapse of the tubular wall structure 34 during torque and advancement forces.

As shown in FIG. 3A, the tubular wall structure 34 includes an elastic outer tubular layer 40 and an inner tubular layer 42 and the distal tip 24. The distal tip 24 generally has a tubular structure with a slightly tapering or frusto-conical distal end. The distal tip 24 includes an outer wall 44, an inner wall 46 and a retainer 48. The outer wall 44 has an axial length longer than the inner wall 46. A proximal end of the outer wall 44 has a tubular shape with straight sides. The outer wall tapers to a neck 52 at its distal free end and begins to flare slightly to a cylindrical bulge 50 moving proximally from the distal free end. The neck 52 has a smaller diameter than the proximal tubular end of the outer wall 44. The proximal tubular end in turn has a smaller diameter than the cylindrical bulge 50.

The inner wall 46 has a shorter axial length than the outer wall but also has a cylindrical shape that tapers—although more gradually—toward its distal free end. An outer surface of the inner wall 46 and inner surface of the outer wall 44 define an annular space 54 which is configured to receive a distal free end of the elastic outer tubular layer 40, as shown in FIG. 3A. The annular space 54 bulges some due to its position subjacent the cylindrical bulge 50 of the outer wall 44. This bulge facilitates insertion and capture of the elastic outer tubular layer. The annular space 54 tapers to a point moving distally as the surfaces of the outer wall 44 and inner wall 46 converge into binding contact.

The retainer 48 is an additional arc-shaped wall that extends along a portion of the inner surface of the inner wall 46 and defines its own crescent-shaped space 56, as shown in the cross section of FIG. 3B. The crescent-shaped space 56 is configured to receive a foldable thin wall portion of the inner tubular layer 42, as will be described in more detail below. The retainer 48 has an arc size that corresponds with a circumferential arc-length of the folded over portion of the inner tubular layer 42 when it is in its compressed or folded configuration. Advantageously, the distal tip 24 helps to increase the structural rigidity of the distal end of the tubular wall structure 34, blocks blood flow between the layers and provides a smooth, tapered profile for pushing through tissue when advanced over a wire or dilator.

Figure 4:
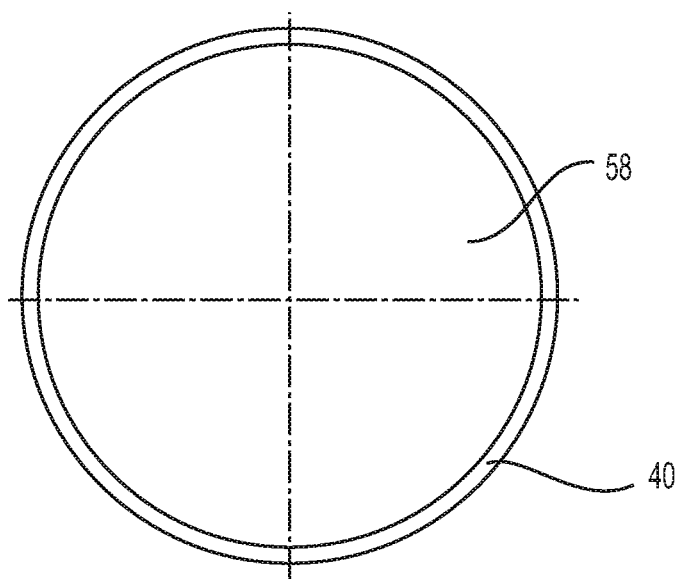
FIG. 4 is a cross sectional view of an exemplary implementation of the outer tubular layer of the sheath.

As shown in FIG. 4, the outer tubular layer 40 of one embodiment has a cylindrical shape with a circular cross-section along its entire length. The outer tubular layer 40 defines an initial elastic lumen 58 extending axially through its cylindrical cross-section. The outer tubular layer is sized to accommodate the delivery passage of the patient and/or the size of the implant 12 to be delivered. For example, the inside diameter, ID, of the layer 40 may be 0.185 inches and may have a wall thickness of 0.005+/−0.001 inches for delivery of a stent-mounted heart valve through transfemoral access. In one aspect, inner surface of the outer tubular layer 40 and/or outer surface of the inner tubular layer 42 may be treated to have or have applied thereto a lubricious coating to facilitate unfolding and folding of the inner tubular layer 42.

The elastic lumen 58 is referred to as "initial" to designate its passive or as-formed diameter or cross-sectional dimension when not under the influence of outside forces, such as the implant 12 passing therethrough. It should be noted, however, that because the outer tubular layer 40 is comprised in the illustrated embodiment by an elastic material it may not retain its shape under even light forces such as gravity. Also, the outer tubular layer 40 need not have a cylindrical cross-section and instead could have oval, square or other cross-sections which generally can be configured to meet the requirements of the inner tubular layer 42 and/or expected shape of the implant 12. Thus, the term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

The outer tubular layer 40, in one implementation, is constructed of a relatively elastic material that has enough flexibility to mediate the expansion induced by passage of the implant 12 and expansion of the inner tubular layer 42 while at the same time having enough material stiffness to urge the inner tubular layer back into an approximation of the initial diameter once the implant has passed. An exemplary material includes NEUSOFT. NEUSOFT is a translucent polyether urethane based material with good elasticity, vibration dampening, abrasion and tear resistance. The polyurethanes are chemically resistant to hydrolysis and suitable for overmolding on polyolefins, ABS, PC, Pebax and nylon. The polyurethane provides a good moisture and oxygen barrier as well as UV stability. One advantage of the outer tubular layer 40 is that it provides a fluid barrier for the pressurized blood. Other materials having similar properties of elasticity may also be used for the elastic outer tubular layer 40.

Figure 5:
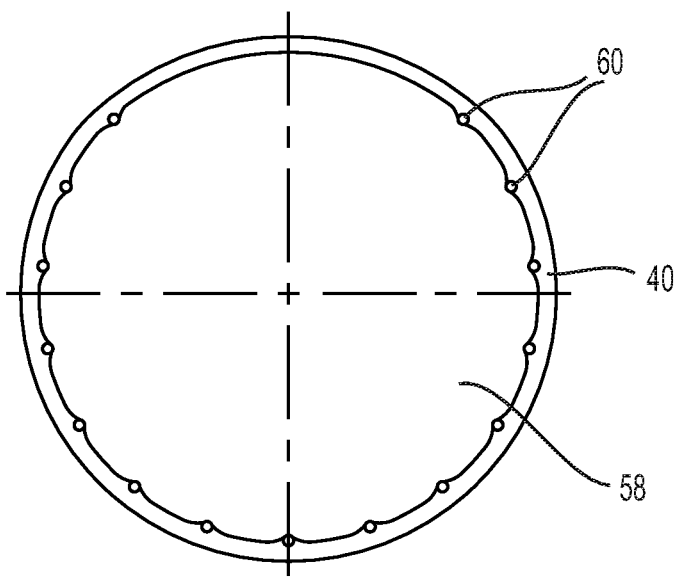
FIG. 5 is a cross sectional view of another exemplary implementation of the outer tubular layer of the sheath.
Figure 6:
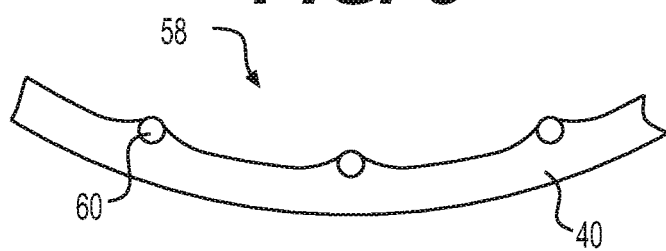
FIG. 6 is a magnified view of part of the outer tubular layer of FIG. 5, showing the cross section of longitudinal rods in greater detail.

FIG. 5 shows another implementation of the elastic outer tubular layer 40 including a plurality of longitudinal rods 60. The longitudinal rods 60 extend the length of the outer tubular layer 40 and protrude into the initial elastic lumen 58. The longitudinal rods 60 are coupled to the outer tubular layer, such as by being co-extruded and/or embedded into the elastic material of the outer tubular layer, as shown in FIG. 6. Advantageously, the longitudinal rods 60 are configured to provide a bearing surface to facilitate relative movement of the inner tubular layer 42 within the outer tubular layer 40. This is especially helpful when the inner tubular layer 42 is unfolding and returning to its originally folded shape.

The longitudinal rods 60 may be circumferentially spaced about the inside surface of the outer tubular layer 60. Although fifteen longitudinal rods 60 are shown in the cross-section of FIG. 5, any number, including a single one, of longitudinal rods may be employed. Also, the longitudinal rods 60 need not extend the entire length of the outer tubular layer 60. They may instead be applied selectively depending upon the demands of the implant, application and other circumstances. Longitudinal rods 60 may be selectively left out of an overall spacing pattern, such as in FIG. 5 where approximately 90 degrees of the inside surface of the outer tubular layer 40 is left as an unadorned surface.

As shown in FIG. 6, the longitudinal rods may have a circular cross-section so as to present a curved bearing surface into the elastic lumen 58. Although diameters for the longitudinal rods 60 may vary, in one embodiment they are 0.004 inches in diameter. The outermost part of the longitudinal rod is positioned about 0.006 inches from the outside surface of the outer tubular layer 40. In this manner, the inner edge surface of the longitudinal rods 60 spaces the inner tubular layer 42 from the surface of the outer tubular layer 40, thus reducing friction or the tendency to stick and impede relative movement. In other embodiments, the longitudinal rods can have other shapes, and the shapes may change within a single rod along the longitudinal direction. As also shown in FIG. 6, the material of the outer tubular layer 40 extends up in a slope past the midpoint of the cross-section of the longitudinal rods 60 for extra stability.

Figure 7:
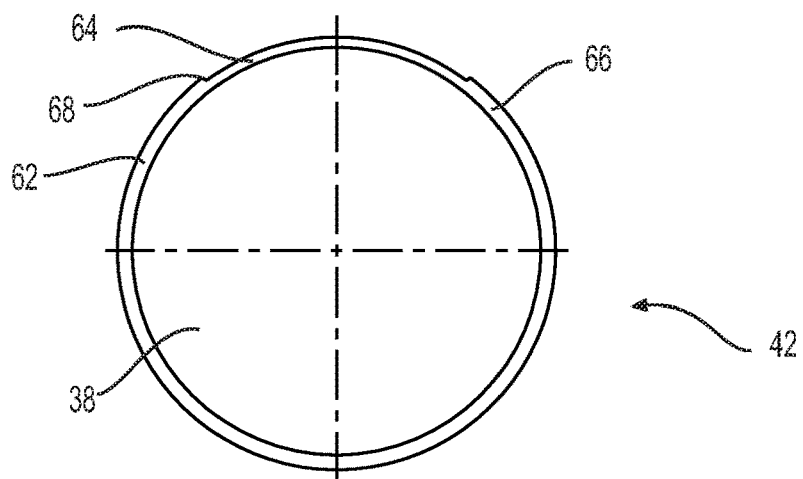
FIG. 7 is a cross section of an exemplary implementation of the inner tubular layer of the sheath.

As shown in FIG. 7, the inner tubular layer 42 has a thick wall portion 62 integrally extruded with a thin wall portion 64. The thick wall portion 62 is approximately 0.011+/− 0.001 inches and the thin wall portion 66 is approximately 0.0065+/−0.0010 inches. The inner tubular layer 42 is preferably constructed of a relatively (compared to the outer tubular layer 40) stiff material such as a stiff polymer like high density polyethylene (HDPE) or an equivalent polymer. Integral construction, such as integral extrusion, of the wall portions advantageously avoids the leakage of prior-art sheaths that use a split in the sheath to promote expandability. Prior-art C-sheaths tend to leak close to the proximal end at the manifold where the sheath is stretched the most. Also, integral construction improves the ability to torque the sheath 8.

The thick wall portion 62, in the illustrated embodiment of FIG. 7, has a C-shaped cross section with a first longitudinally extending end 66 and a second longitudinally extending end 68. The ends are where the thickness of the thick wall portion 62 starts to narrow to thin portion 64 on the cross-section. That transition extends longitudinally in the direction of the axis of the sheath 8, such that the thick wall portion 62 forms an elongate C-shaped channel.

From those ends 66, 68 of the thick wall portion 62 extends the thin wall portion 64 and together they define a tubular shape. Extending longitudinally in that tubular shape is the central lumen 38. FIG. 7, in particular, shows the central lumen 38 in its expanded diameter which is larger than the initial diameter of the elastic outer tubular layer 40. For example, the inner tubular layer 42 has a central lumen 38 that is about 0.300+/−0.004 inches. The outer tubular layer 40 has an initial elastic lumen 58 of about 0.185 inches.

Figure 8:
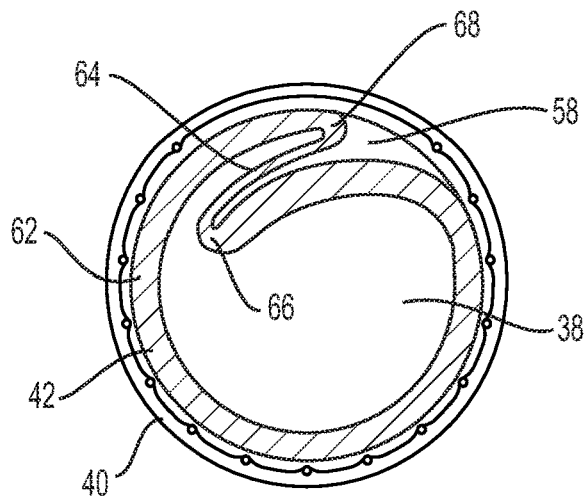
FIG. 8 is a cross section of both the inner and outer tubular layers of the sheath. In this example, the inner tubular layer is in the compressed condition.
Figure 9:
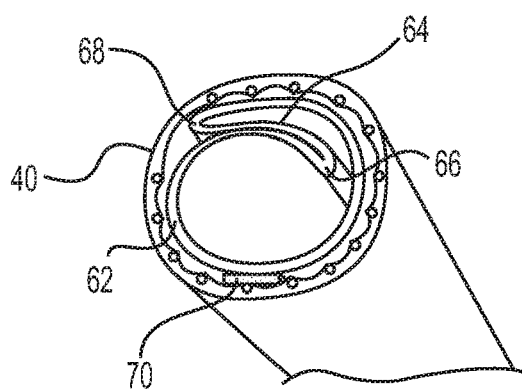
FIG. 9 is a perspective view of the distal end of an implementation of the expandable sheath.

FIGS. 8 and 9 show the inner tubular layer 42 in its compressed or folded condition, folded up and fit into the initial elastic lumen 58 of the outer tubular layer. In the compressed condition, the elastic outer tubular layer 40 urges the first longitudinally extending end 66 under the second longitudinally extending end 68 of the inner tubular layer 42. This positions the thin wall portion 64 between the first and second longitudinally extending ends 66, 68.

Figure 10:
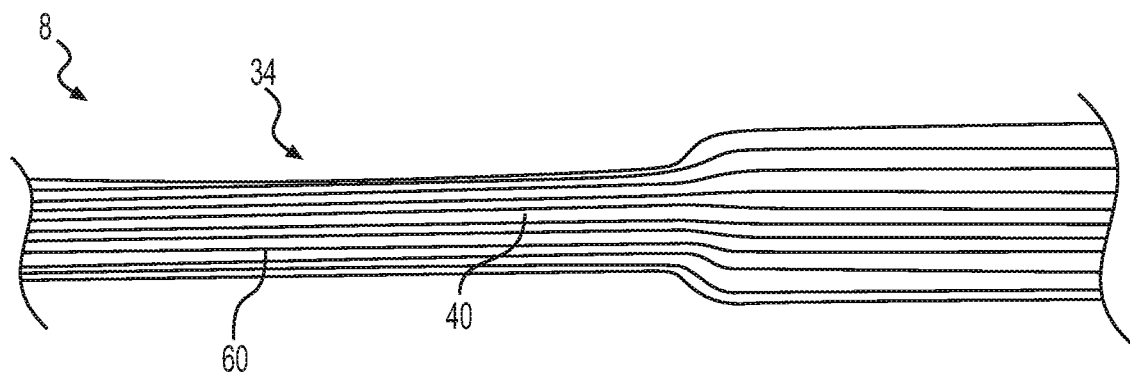
FIG. 10 is a side view of one implementation of the expandable sheath.

FIG. 10 shows a side view of an implant moving through sheath 8. During passage of an implant through the central lumen 38, the tubular wall structure 34 takes on a locally expanded condition corresponding to the length and geometry of the implant 12. In the expanded condition, the first and second longitudinally extending ends 66, 68 radially expand apart, against the urging of the elastic outer tubular layer 40 by passage of the implant 12, into a non-overlapping condition with the thin wall portion 64 extending therebetween to form the expanded lumen, as in FIG. 7. After passage of the implant 12, the inner tubular layer 42 is urged by the outer elastic tubular layer 40 into the compressed condition shown in FIGS. 8 and 9. With this configuration, a 14 French sheath 8 allows passage of a 29 mm transcatheter heart valve, such as the Sapien XT and Sapien 3 transcatheter heart valves available from Edwards Lifesciences.

As another option, the inner tubular layer 42 may be adhered along one or more longitudinally extending portions of the outer tubular layer 40. Adhesion may be by heat fusion between the two layers or adhesive bonding, for example. As shown in FIG. 9, the longitudinally extending portion can be a strip 70 where the outer surface of the inner tubular layer 42 is bonded or otherwise adhered to the inner surface of the outer tubular layer 40. Preferably, the strip 70 is positioned opposite the thin wall portion 64 to be away from, and not affect, the fold of the inner tubular layer 42. Inhibiting folding would also raise the push force for passage of the implant 12. Another implementation may include a second thin bonding strip 70 or line. Although the thickness of the strip 70 can vary, preferably it is relatively narrow to reduce its inhibition of expansion of the two layers and any increases in pushing force. Use of a narrow bonding line between the layers 40, 42 prevents free rotation of the layers with respect to each other while minimizing the effect on push force.

Figure 11:
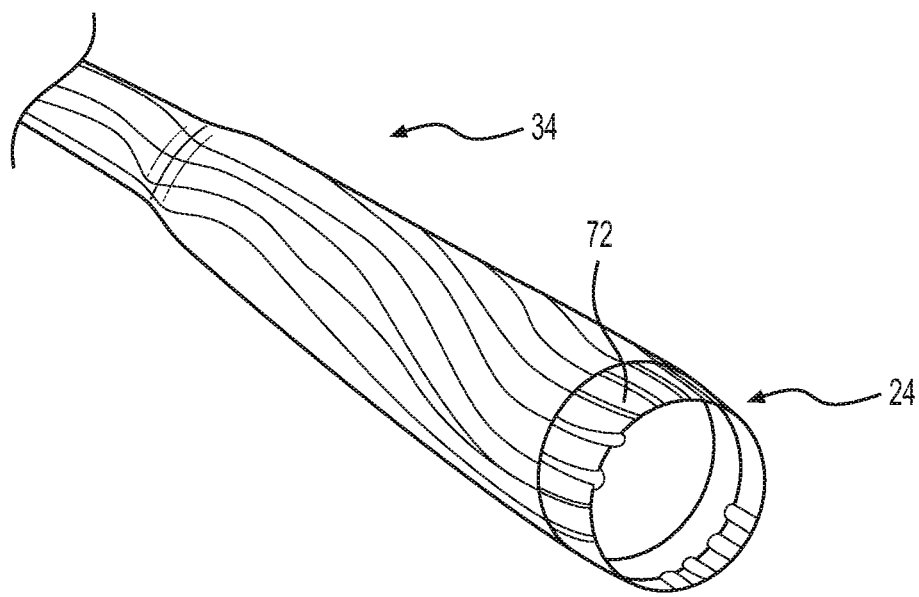
FIG. 11 is a perspective view of one embodiment of a flared distal portion of the sheath.
Figure 14:
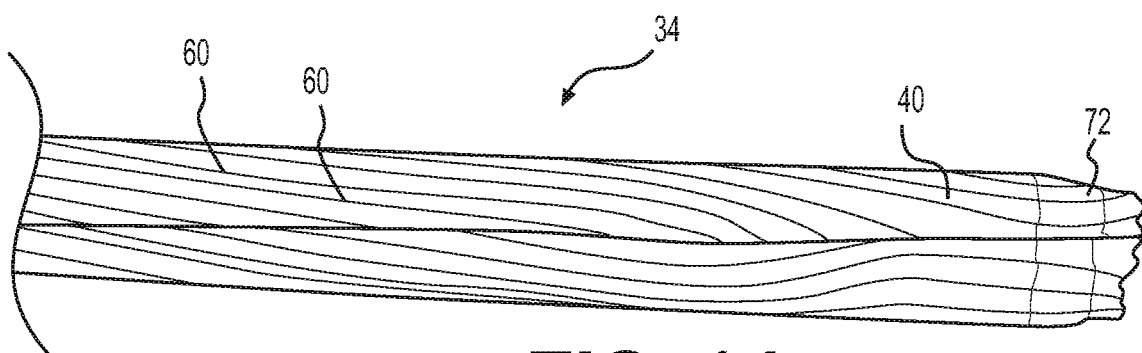
FIG. 14 shows an example flared distal portion of a sheath in a folded configuration.
Figure 15:
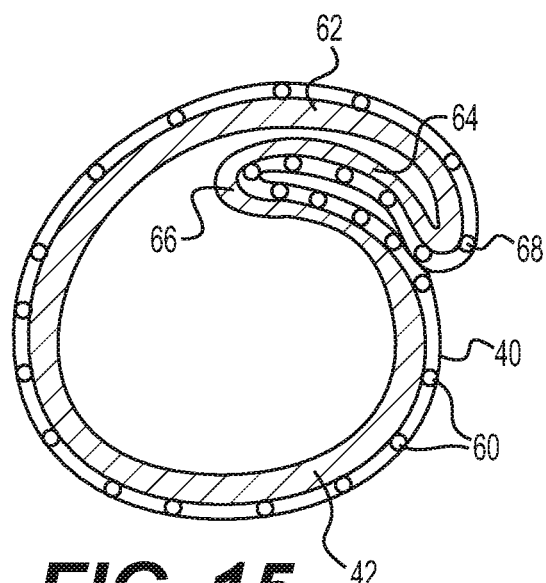
FIG. 15 shows a cross section of a distal portion of a sheath in a folded configuration.
Figure 16:
FIG. 16 shows a sheath during passage of an implant. The inner and outer tubular layers are adhered together in a longitudinally extending strip.

In another embodiment, as shown in FIGS. 11-15, the distal tip 24 of sheath tubular wall structure 34 can be a sealed tip to mitigate blood intrusion and/or facilitate expansion at the distal end of travel of the implant 12. In one aspect, a distal portion of the tubular wall structure 34 may be reflowed to adhere the inner and outer layers 40, 42, as shown in FIG. 11. In particular, the two layers 40, 42 are urged into their fully expanded (unfolded condition) and then reflowed to bind the outer surface of the inner tubular layer 42 to the inner surface of the outer tubular layer 40. Then, the reflowed portion is returned to the compressed or folded configuration and compressed under a heat shrink layer 74 to set the fold. The heat shrink layer 74 is then removed. Thus, when the distal end of the wall structure 34 folds, the outer tubular layer 40 is also folded, as shown in FIGS. 14 and 15. Sealing the tip stops blood from getting between the two layers 40, 42 at the distal end of the sheath 8 while maintaining the highly expandable performance of the tubular wall structure 34.

Figure 12:
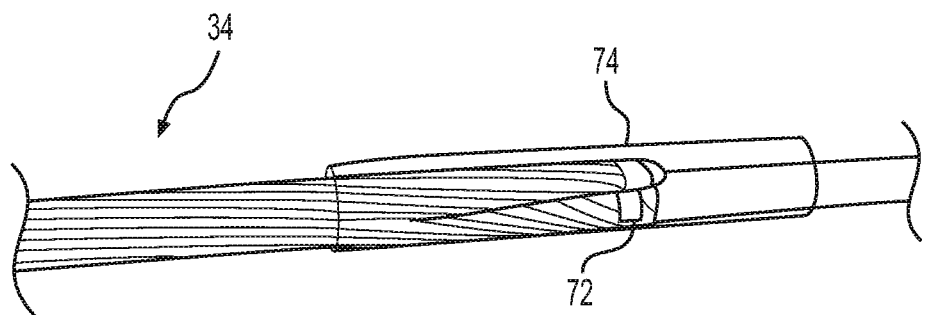
FIG. 12 shows a side view of the distal portion of a sheath folded in a heat-shrink tube.
Figure 13:
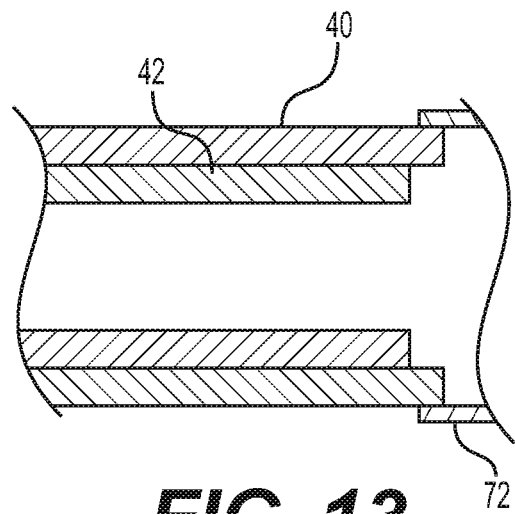
FIG. 13 shows a longitudinal cross section of an embodiment of the distal portion of the sheath including a radioopaque tubular layer.

The reflowed outer tubular layer 40 may have added thereto a radiopaque ring 72. The radiopaque ring 72 can be adhered outside (such as by heat shrinking) and around the reflowed, folded distal portion of the outer tubular layer 40. The ring 72 may be applied (such as by reflowing) outside the outer tubular layer 40 (FIG. 13) or inside the outer tubular layer 40 (FIG. 12). The ring 72 is preferably constructed of a highly elastic polymer to allow expansion and facilitate urging the tip back into a folded configuration.

Advantageously, the outer tubular layer 40 and inner tubular layer 42 are both seamless, which stops blood leakage into the sheath 8. The seamless construction of the inner tubular layer 42 eliminates the ends of a conventional C-sheath. Elimination of the cut in the C-sheath by addition of thin portion 64 improves torque performance. Also, both layers are easily manufactured by an extrusion process. The elastic outer tubular layer 40 has an elastic material that is similar to or the same as most soft tips, making their attachment much easier.

Figure 17:
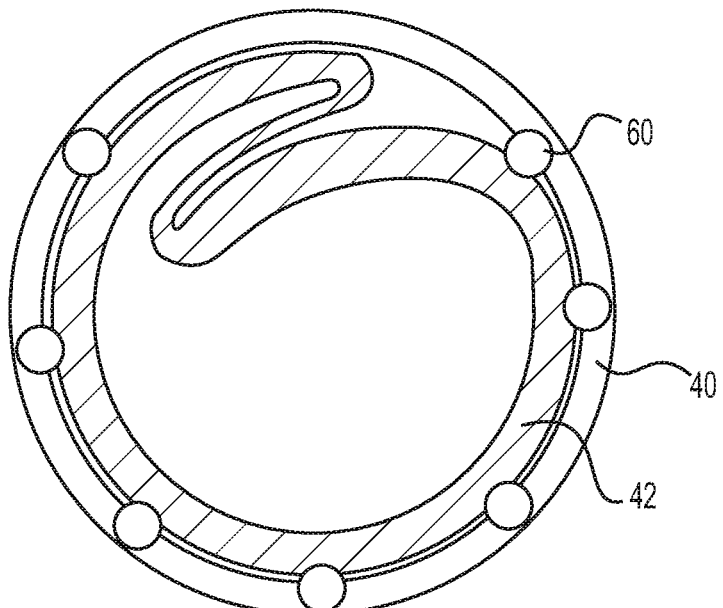
FIG. 17 shows a cross section of an exemplary embodiment including longitudinal rods embedded in the outer tubular layer and protruding into the elastic lumen.
Figure 18:
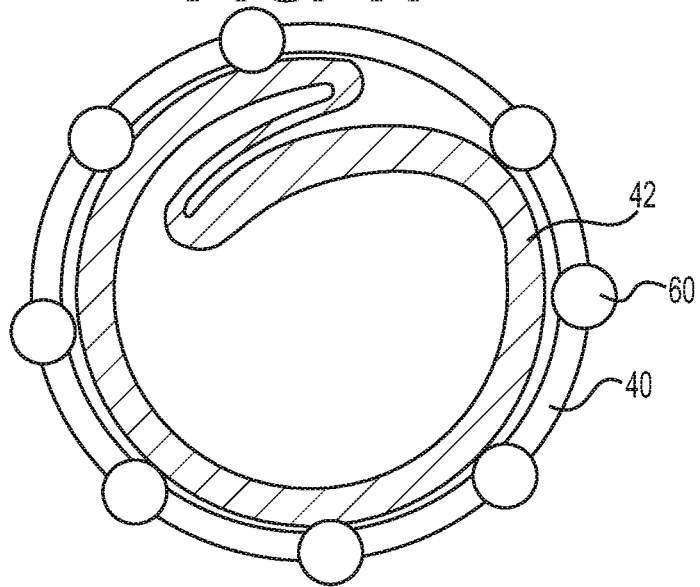
FIG. 18 shows a cross section of an exemplary embodiment including longitudinal rods embedded in the outer tubular layer and protruding into the elastic lumen and outward from the outer surface of the outer tubular layer.

As shown in FIGS. 17-20, other embodiments of the sheath 8 may include a conventional C-shaped inner tubular layer 42 surrounded by an elastic outer tubular layer 40 employing longitudinal rods 60. (FIGS. 17-20 may also use other types of inner tubular layer 42, such as the integrally formed ones disclosed herein.) FIG. 17 shows use of seven longitudinal rods equally spaced from each other about the interior surface of the outer tubular layer 40 with the exception that a rod is missing from a portion adjacent a split in the inner tubular layer 42. This gap facilitates distraction and return of the free edges of the C-shaped inner tubular layer 42. FIG. 18 shows a similar arrangement but with the eighth longitudinal rod 60 present. But the rod is somewhat offset from the location of the free edges of the inner tubular layer 42. Furthermore, the rods of FIG. 18 protrude outward from the outer surface of the outer tubular layer 40 to lower friction between the sheath and, for example, a body lumen or an additional outer delivery sheath.

Figure 19:
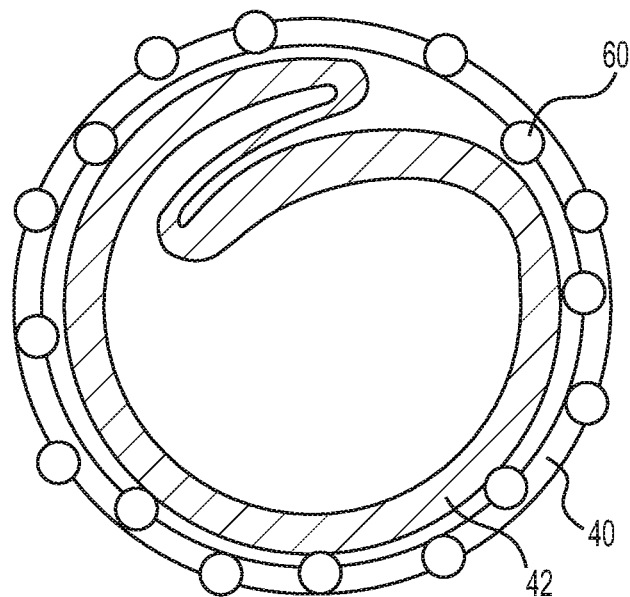
FIG. 19 shows a cross section of an exemplary embodiment including longitudinal rods embedded in the outer tubular layer, where some rods protrude into the elastic lumen and others protrude outward from the outer surface of the outer tubular layer.
Figure 20:
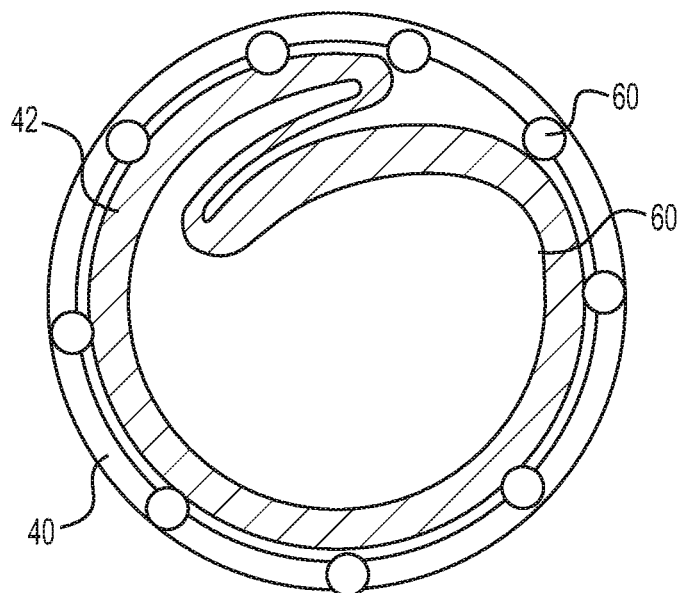
FIG. 20 shows a cross section of an exemplary embodiment including longitudinal rods embedded in the outer tubular layer and the inner tubular layer. The longitudinal rods embedded in the outer tubular layer protrude into the elastic lumen and the longitudinal rods embedded in the inner tubular layer protrude into the central lumen.

FIG. 19 shows another embodiment wherein rods are embedded in the outer tubular layer 40 and extend from the inside and outside surfaces thereof in alternation. This can lower friction from advancement of the sheath 8 wherein, for example, the outer surface of the layer 40 touches a body lumen or additional outer delivery sheath. FIG. 20 shows another embodiment wherein the inner tubular layer 42 also includes a plurality of longitudinal rods 60 that facilitate, for example, easy passage of the implant 12.

The outer tubular layer 40 in the configurations of FIGS. 17-20 still can have a highly elastic, thin structure to fit over the conventional C-sheath inner tubular layer 42. As the outer tubular layer 40 is not adhered to the inner tubular layer 42, there is free movement between the sleeve and the delivery catheter 10. The outer tubular layer 40 is also seamless to guard against blood leakage. The sheath 8 is stretched evenly along all segments in a radial direction—reducing the risk of tearing or fracture. And, the elastic outer tubular layer 40 will urge the C-shaped sheath back into the reduced profile configuration. During construction, the inner layer 42 is easily fitted inside the outer layer 40 without flattening or heat wrapping. Implementations may include a large number of longitudinal rods 60—even 100 or more depending upon their cross-sectional size. The longitudinal rods 60 may include microstructure patterns that further reduce friction.

Figure 21:
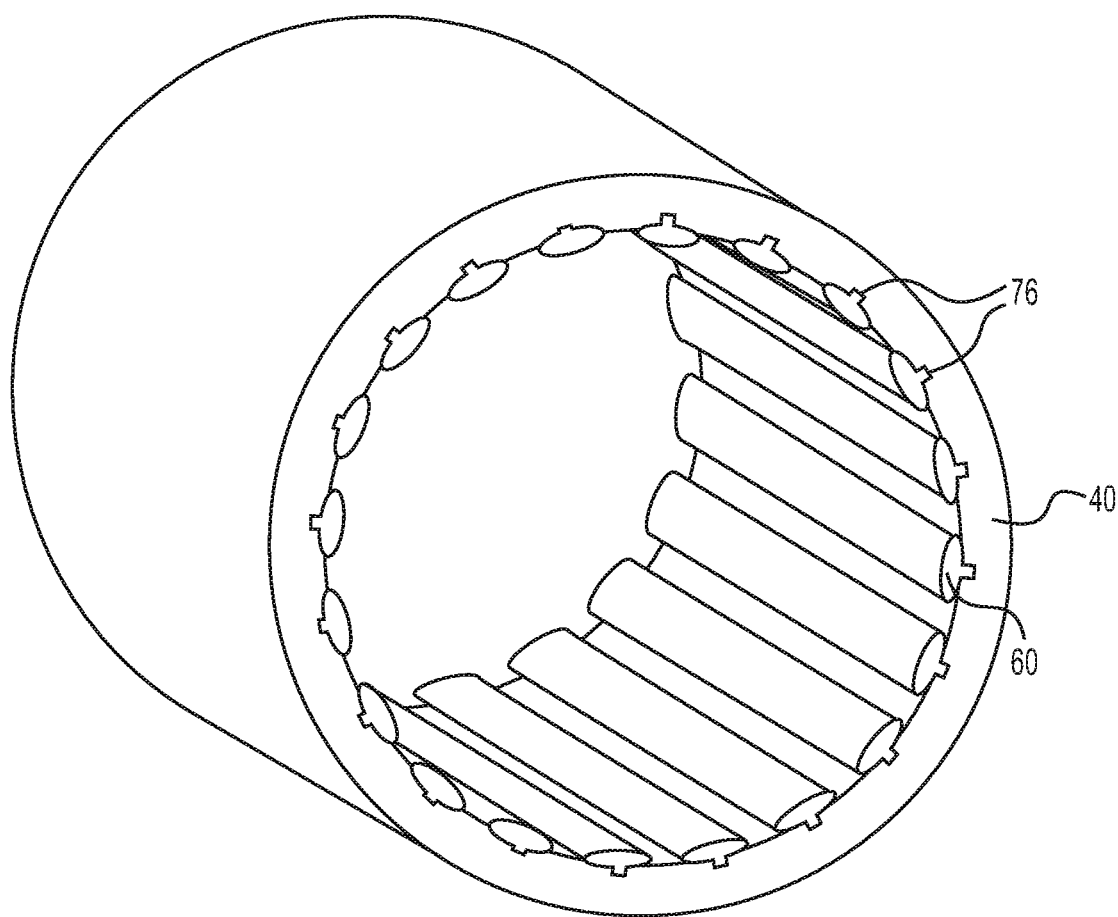
FIG. 21 shows a cross section of another exemplary embodiment including longitudinal rods embedded in the outer tubular layer and protruding into the elastic lumen.
Figure 22:
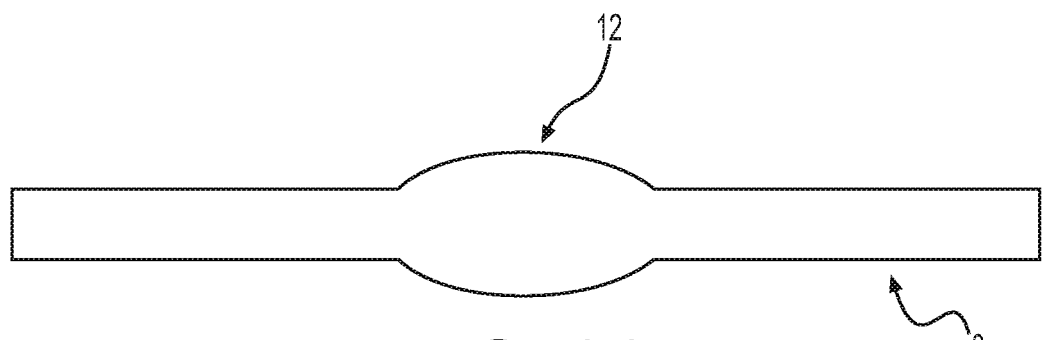
FIG. 22 shows a side view of the sheath with an implant passing therethrough.

FIGS. 21 and 22 show yet another embodiment of the sheath 8 including a segmented outer tubular layer 40 having longitudinal rods 60 that may be employed with or without an inner tubular layer 42. As shown in FIG. 21, the outer tubular layer 40 has elongate cuts or grooves that form elongate segments 76 extending axially along inner surface. Formed or mounted along the grooves are the longitudinal rods 60. The longitudinal rods 60 are shown in FIG. 21 to have curved or arc-shaped top surfaces that reduce friction for passing implants 12. The longitudinal rods 60 are comprised of relatively high stiffness materials such as HDPE, fluropolymer and PTFE. The outer tubular layer 40 can be constructed of highly elastic materials with a low tensile set (TPE, SBR, silicone, etc.) to facilitate recovery after expansion. When used without an inner tubular layer 42, the outer tubular layer 40 can have additionally lowered expansion force—especially because the higher strength material (the rods) are not connected in the radial direction. Other variations may include changing the number and shape of the rods 60, incorporation of a tie layer or undercut/bard to strengthen the connection of the rods to the outer layer 40 and adding sections of stiff material to the outside of the outer layer for improved stiffness and pushability. A slip additive may be applied to the surfaces to increase lubricity. FIG. 22 shows the bulge in the sheath 8 as the implant 12 passes therethrough.

Figure 23:
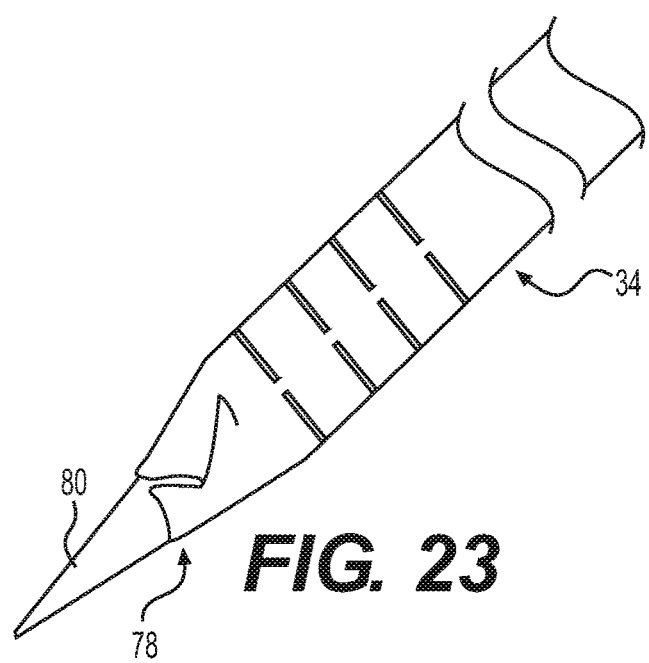
FIG. 23 shows a flared implementation of a distal portion of the sheath, where the flared portion is folded into a compressed configuration.
Figure 24:
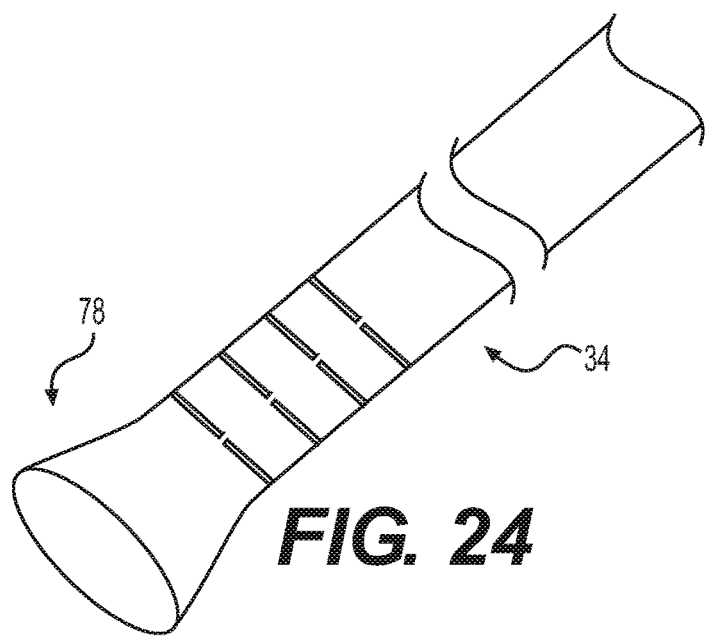
FIG. 24 shows the distal portion of FIG. 23 with the flared portion unfolded and expanded.
Figure 25:
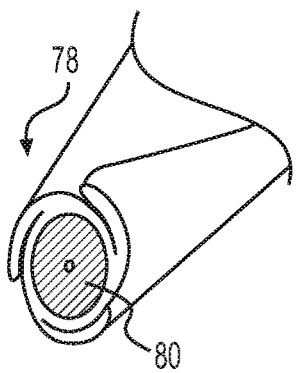
FIG. 25 shows a cross section of the distal portion of FIG. 23, where the flared portion is folded into a compressed condition.

FIGS. 23-25 show another embodiment wherein a distal end of the tubular wall structure 34 can have a flared portion 78. The flared shape of the flared portion 78 helps to reduce snags or interference during retrieval experienced with conventional sheaths during retrieval of medical devices. The flared portion 78 is folded or wrapped around the tapered distal end of an introducer 80 to maintain a low profile for advancement, as shown in FIGS. 23 and 25. The number and size of the folds may vary depending upon the size and material type of the tubular wall structure 34. For example, FIG. 25 shows three folds in a cross-sectional view. After the distal end of the sheath 8 is in position, the introducer 80 is removed. Then, the sheath 8 is ready to receive the delivery catheter 10 and implant 12. When the implant 12 reaches the flared portion 78 the folds then break and expand into the flared configuration, as shown in FIG. 24. The flared portion 78 remains in this flared configuration for possible retrieval of the implant 12.

Figure 28:
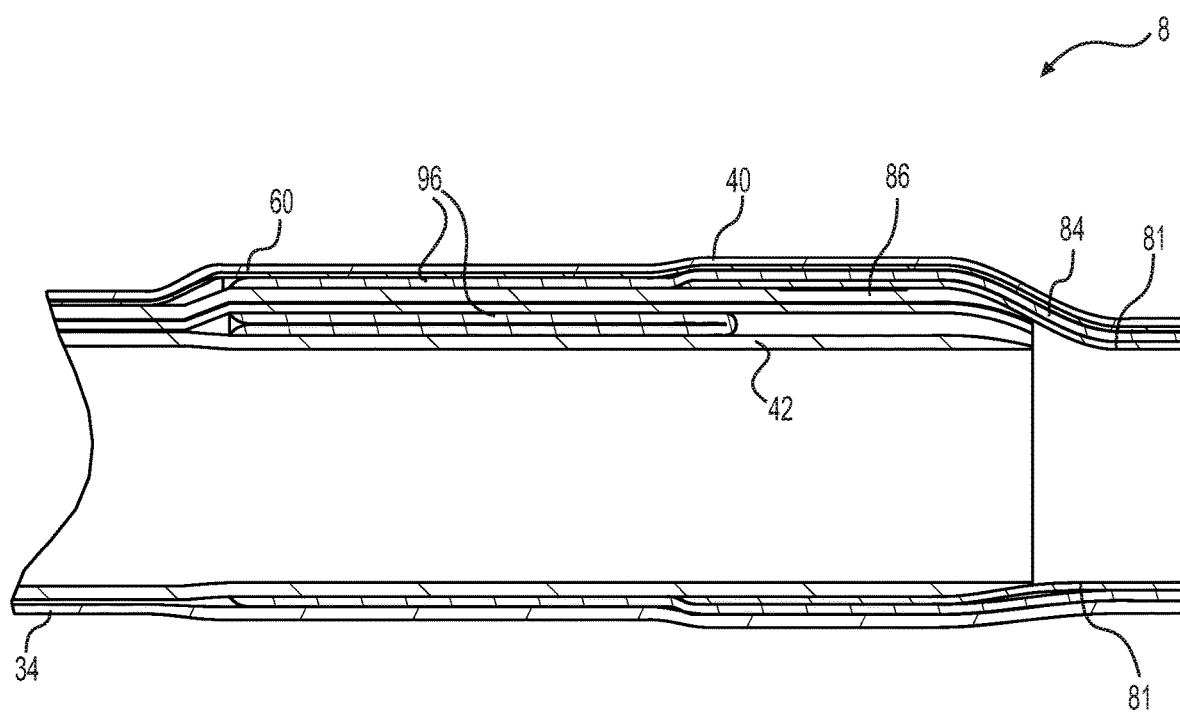
FIG. 28 shows a longitudinal cross section of the distal region of the implementation shown in FIG. 26.
Figure 29:
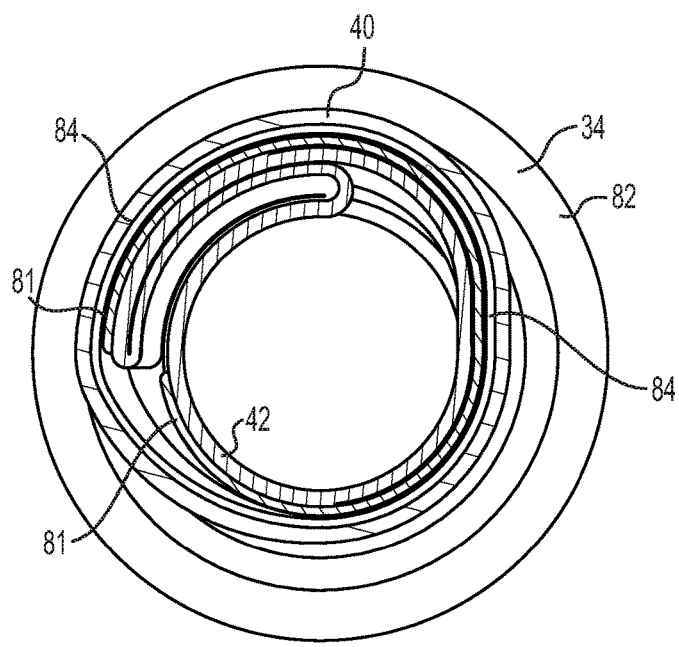
FIG. 29 shows a cross section of the distal region of the implementation shown in FIG. 26.

FIGS. 26-29 show another embodiment of the sheath 8. The sheath 8 includes the tubular wall structure 34 that extends from the proximal end (as shown in cross-section in FIG. 27) to the distal end (FIGS. 28 and 29). Generally, the tubular wall structure 34 includes inner tubular layer 42, inner tip layer 81, strain relief tubular layer 82, outer tip layer 84 and the elastic outer tubular layer 40.

Figures 26, 27:
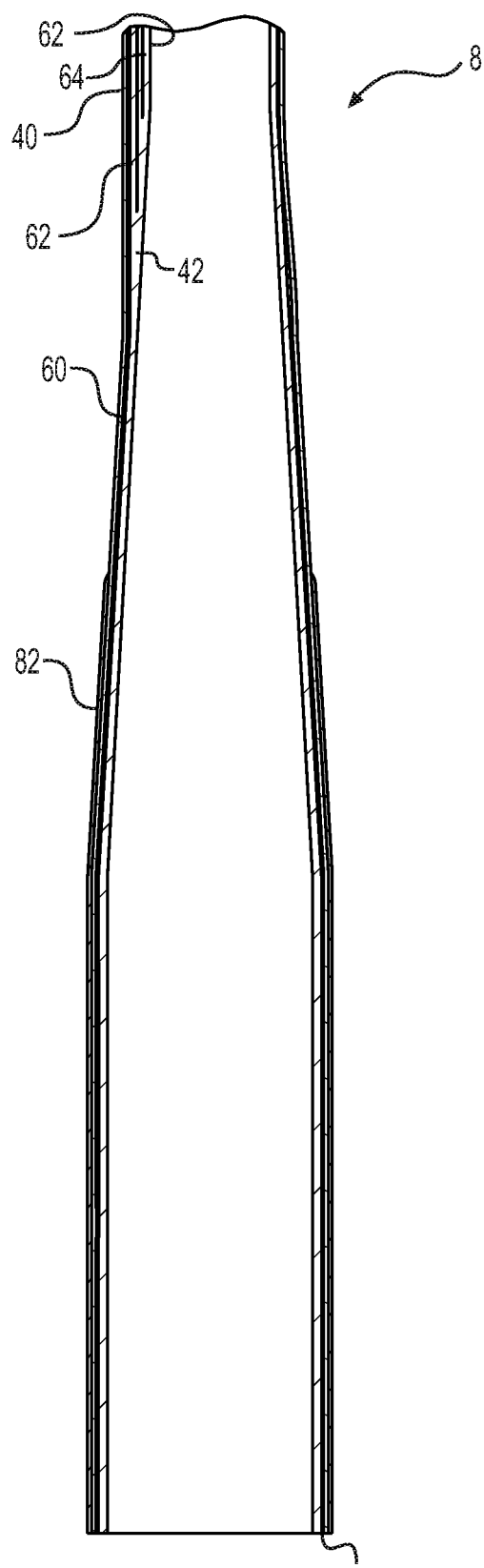
FIG. 26 shows a perspective view of an exemplary implementation of the expandable sheath.
FIG. 27 shows a longitudinal cross section of the proximal region of the implementation shown in FIG. 26.

As can be seen the tubular wall structure 34 has different layers depending up on the axial position. The wall structure 34 includes a strain relief tubular layer 82 that terminates about ⅔ of the way from the proximal end, as shown in FIG. 27. The strain relief layer 82 is preferable comprised of a relatively stiff material, such as HDPE, that can withstand the strains of the proximal end of the sheath 8 where it is joined to the hub and 20 and other components for accepting initial insertion of the delivery apparatus 10. It terminates short of the distal end of the sheath 8 to facilitate a greater flexibility and lower profile of the distal end of the sheath 8.

Extending past the strain relief tubular layer 82 the tubular wall structure 34 drops down to two layers, the inner tubular layer 42 and elastic outer tubular layer 40. On the proximal-most end of the portion of the sheath 8 shown in FIG. 27, the inner tubular layer splits (in cross-section) into its thick wall portion 62 and thin wall portion 64 in the folded over configuration.

At the distal end, as shown in FIGS. 28 and 29, the sheath 8 includes tip structure (including inner tip layer 81 an outer tip layer 84) configured to taper the wall structure 34 and seal the free end of the layers against blood or fluid invasion. Generally, these components build up the diameter of a length of the wall structure 34 with some additional layers including stiffening layers, and then tapers out and over the distal free end of the inner tubular layer 42.

The inner tubular layer 42 is similar to that described above. It includes the thin wall portion 64 that is configured to fold over into the folded configuration back onto the thick wall portion 62. Also, the elastic outer tubular layer 40 restrains the inner tubular layer 42 against expansion. But, the elasticity of the outer tubular layer 40 can also be overcome to allow the inner tubular layer to at least partially unfold into a wider central lumen 38 for passage of the implant 12 or other device.

As shown in FIG. 28, the inner tip layer 81 extends only a short axial length. In particular, the inner tip layer 81 extends around and past the distal-most end of the foldable inner tubular layer 42, tapering into smaller diameter free end after extending distally past the free end of the foldable inner tubular layer. As shown in the cross-section orthogonal to the long axis of the sheath 8 of FIG. 29, the inner tip layer 81 has a C-shaped cross-section. (The top of the C-shape is enlarged somewhat to account for the overlapping layers of the wall structure 34—so that the free longitudinal edges are radially spaced apart to form a gap.) The C-shaped cross-section allows the free longitudinal edges of the inner tip layer 81 to spread apart during unfolding of the inner tubular layer 42. Advantageously, the inner tubular layer 42 has a relatively stiff material construction smoothing, stiffening and tapering the distal end of the sheath 8 as well as providing some protection for the free end of the inner tubular layer 42. The inner tip layer 81 also advantageously extends over the distal end of the inner tubular layer 42, thereby sealing the thick and thin wall portions 62, 64 against blood and fluid invasion.

The outer tip layer 84 extends over and is adhered to the inner tip layer 81 and a distal portion of the inner tubular layer 42. The outer tip layer 84 covers the proximal edge of the inner tip layer 81, sealing it against the inner tubular layer 42. The outer tip layer 84 is of a relatively bendable material and, where it is directly adhered to the thin wall portion 64, can be folded over onto itself as shown in FIG. 28. Advantageously, then, the outer tip layer 84 tracks the unfolding of the thick and thin wall portions 62, 64 to continue to seal the inner tip 81 to the inner tubular layer 42. Notably, as the outer tip layer 84 unfolds the free longitudinal edges of the C-shaped inner tip layer 81 can come apart for coordinated lumen expansion of the sheath 8. But, also, at the same time the stiffness of the inner tip layer 81 and extra reinforcement of the outer tip layer 84 help to maintain tip stiffness and stability.

The elastic outer tubular layer 40 extends all the way to the distal end of the sheath 8, including over the distal end of the outer tip layer 84. In addition, the inside of the elastic outer tubular layer includes rods 60 extending axially and reducing unfolding resistance by lowering surface area and increasing lubricity.

The sheath 8 may also include a radiopaque marker band or layer portion 86 that provides an orientation and depth indication under radioscopy during implantation or other medical procedures.

Figure 30:
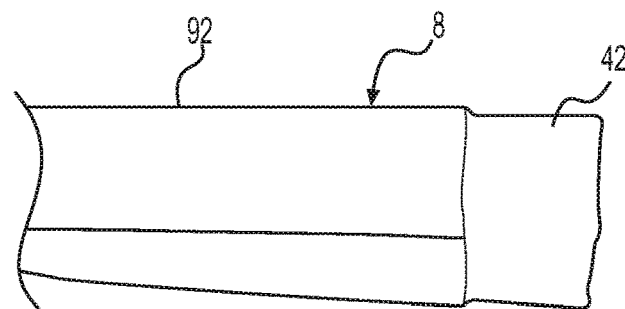
FIGS. 30 through 38 show a method of assembling a stiffened and sealed tip for another embodiment of the expandable sheath.
Figure 31:
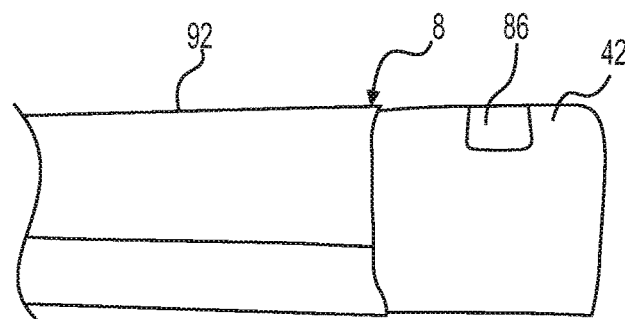

FIGS. 30 through 38 show a method of assembling a stiffened and sealed tip for another embodiment of the sheath 8. FIGS. 30-38 show varying views of the same sheath 8 as it undergoes the method of assembly. FIGS. 30 and 31 show the inner tubular layer 42 (to the right) in the unfolded configuration. An additional tubular layer 92 (such as a strain relief or elastic layer) (to the left) extends over the inner tubular layer 42 but stops short of the free end of the inner tubular layer. FIG. 31 shows a portion of the radiopaque marker 86 attached to the inner tubular layer 42.

Figure 32:
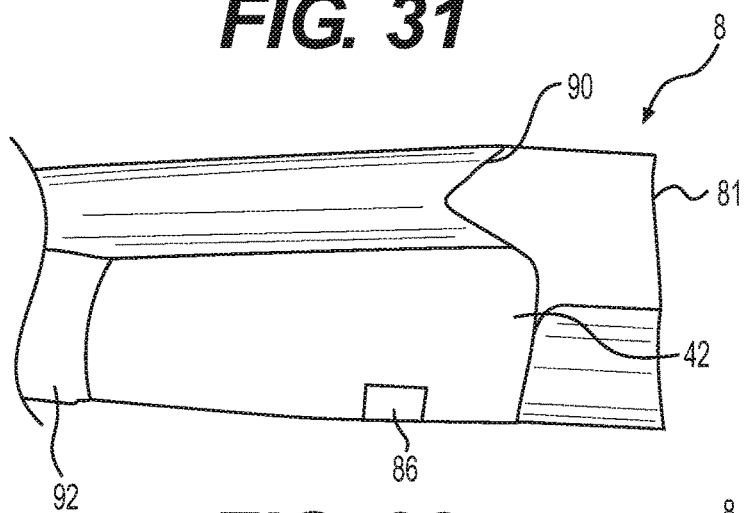
Figure 33:
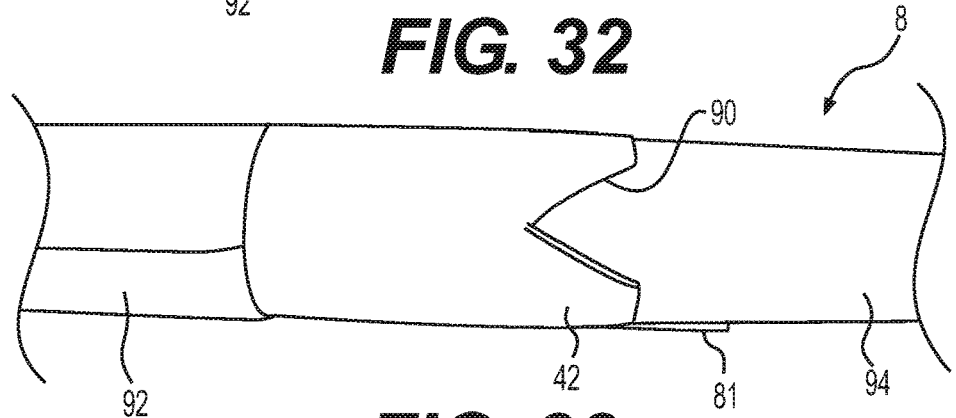

FIG. 32 shows the inner tubular layer 42 with a window or v-shaped notch 90 cut into its free end to allow for tip expansion. The v-shaped notch 90 also facilitates retrieval of an implant. FIG. 32 also shows the C-shaped inner tip layer 81 extended around an outside of the inner tubular layer. FIG. 33 shows a second notch 90 on the opposite side of the inner tubular layer 42. Also in FIG. 33, the distal tip of the partially constructed sheath 8 is extended over a mandrel 94 to facilitate folding and attachment of other layers.

Figure 34:
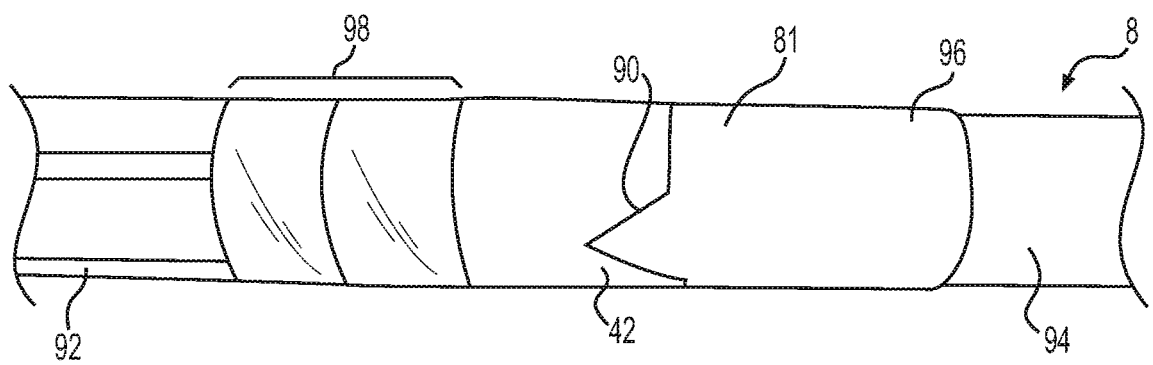

FIG. 34 shows formation of a proximal hemostasis seal by application of a proximal sealing layer 96 that extends around a distal free end of the additional tubular layer 92 and over and past the distal end of the emerging inner tubular layer 42. In the embodiment shown in FIG. 34, the proximal sealing layer 96 is transparent such that the v-shaped notch 90 is visible from underneath the sealing layer 96. A proximal section 98 of the sealing layer 96 is heat treated to seal the transition between the additional tubular layer 92 and the inner tubular layer 42, which in some embodiments can give proximal section 98 a glossier appearance than the remainder of sealing layer 96. The proximal section 98 blocks blood and other fluids from entering between the two layers 42, 92.

Figure 35:
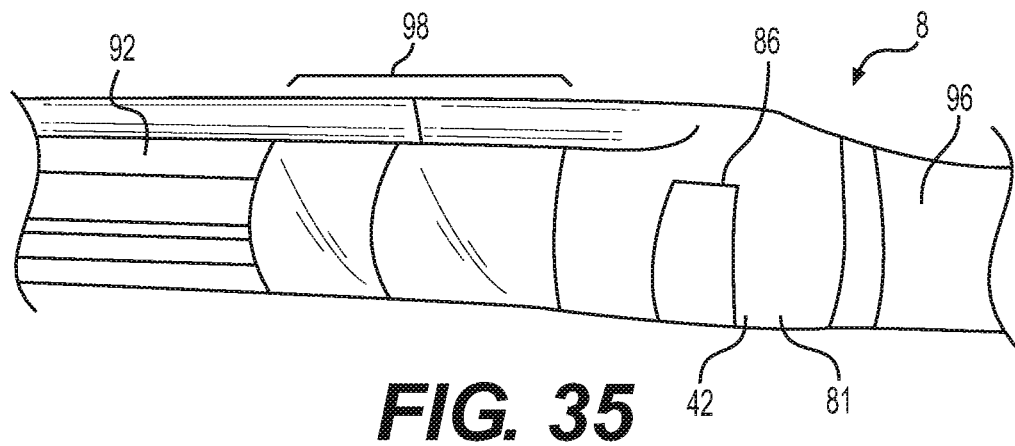
Figure 36:
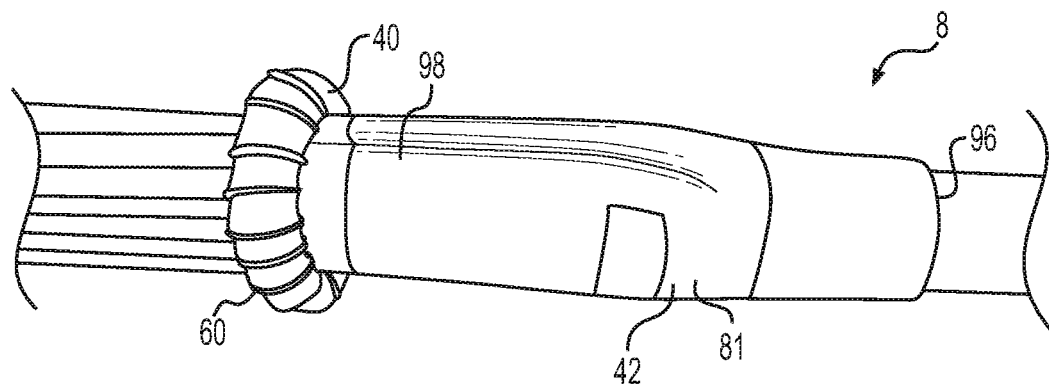
Figure 37:
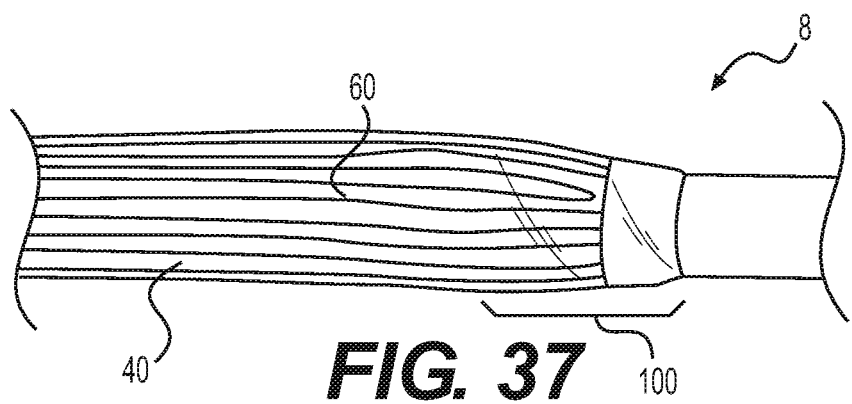
Figure 38:
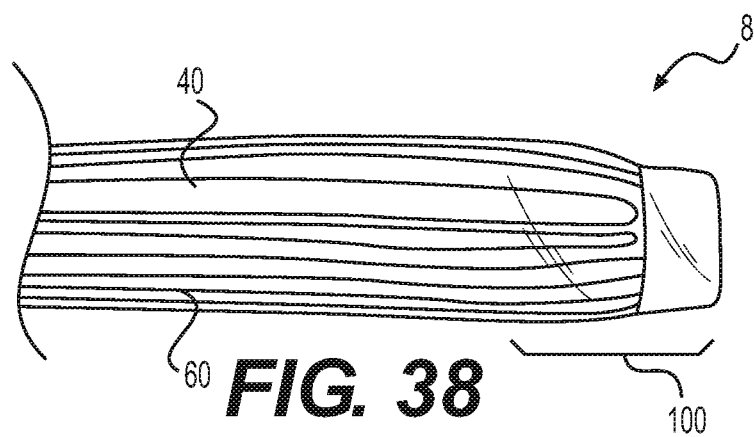
Figure 39:
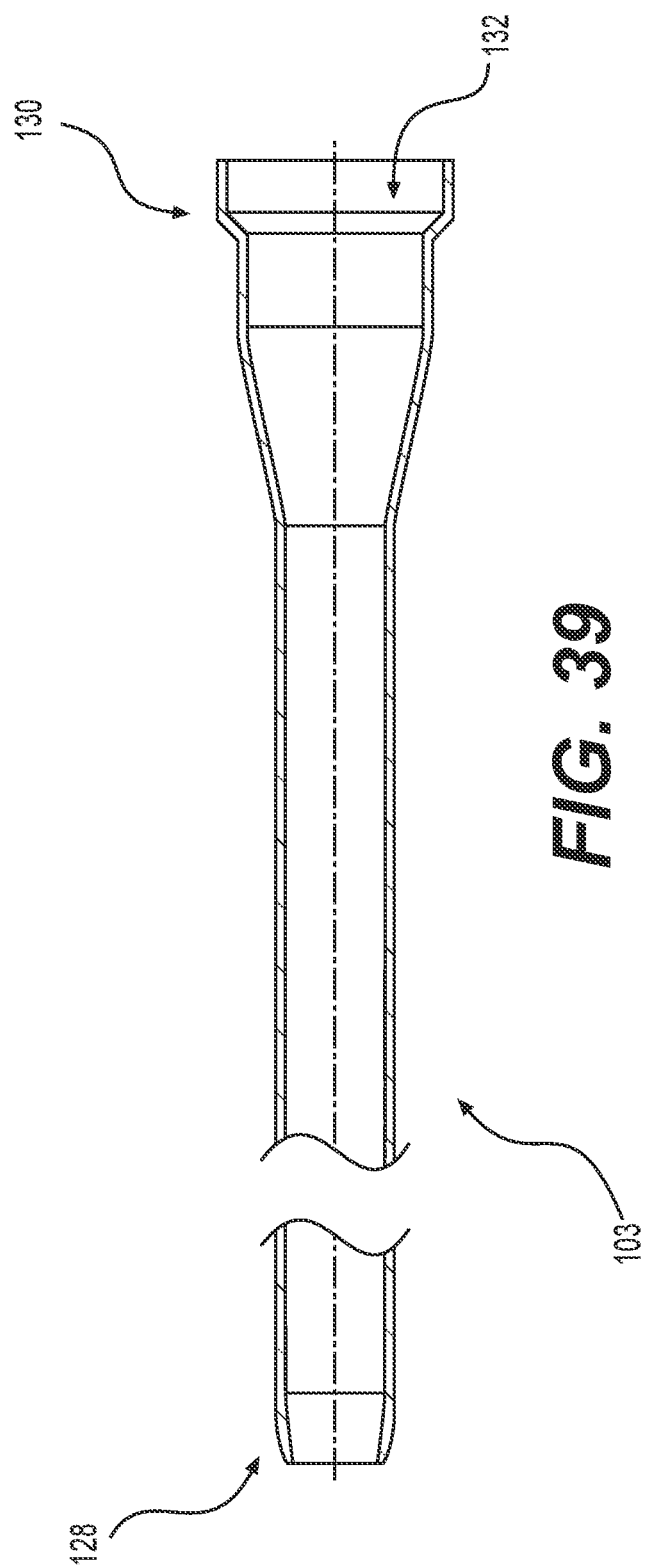
FIG. 39 is a cross-sectional view of a sheath of one embodiment of the present invention.

FIG. 35 shows the layers 42, 92 and 96 being folded over onto themselves. FIG. 36 shows the elastic outer tubular layer 40 or jacket with rods 60 being unrolled over the now folded layers 42, 92 and 96. FIG. 37 shows the outer tubular layer 40 itself slightly folded at the distal end and having applied thereover a distal sealing layer 100. The excess of the free end of the proximal sealing layer 96 extending past the distal sealing layer 100 is cut away. The distal sealing layer advantageously urges the distal free end of the layers 40, 42 and 96 into a tapered configuration and provides a rounded distal end for the tubular wall structure 34 that facilitates insertion and advancement over the guidewire.

FIGS. 39-42 show one embodiment of sheath 103 including a wall structure having a tip 128 on its distal end and a flared portion on its proximal end 130 and defining a lumen 132 extending therebetween. The wall structure includes an outer elastic layer 120, an intermediate mesh layer 122, a mixed expandable layer 124 and an inner lubricious low-friction liner or layer 126. Generally, the flared proximal end 130 is sized and shaped to accept a distal male end of a hub structure containing, among other things, a hemostasis valve to mediate leakage during insertion of delivery catheters through the lumen 132 of the delivery sheath 103. The sheath 103 can be sized for delivery of prosthetic implants in the form, for example, of stent-mounted soft-tissue heart valves. For such an application, the sheath can have an outside diameter 0.260 inches and an inside diameter of 0.215 inches. Those diameters can vary with the size of the implant and/or the type of implant or other application.

Figure 41:
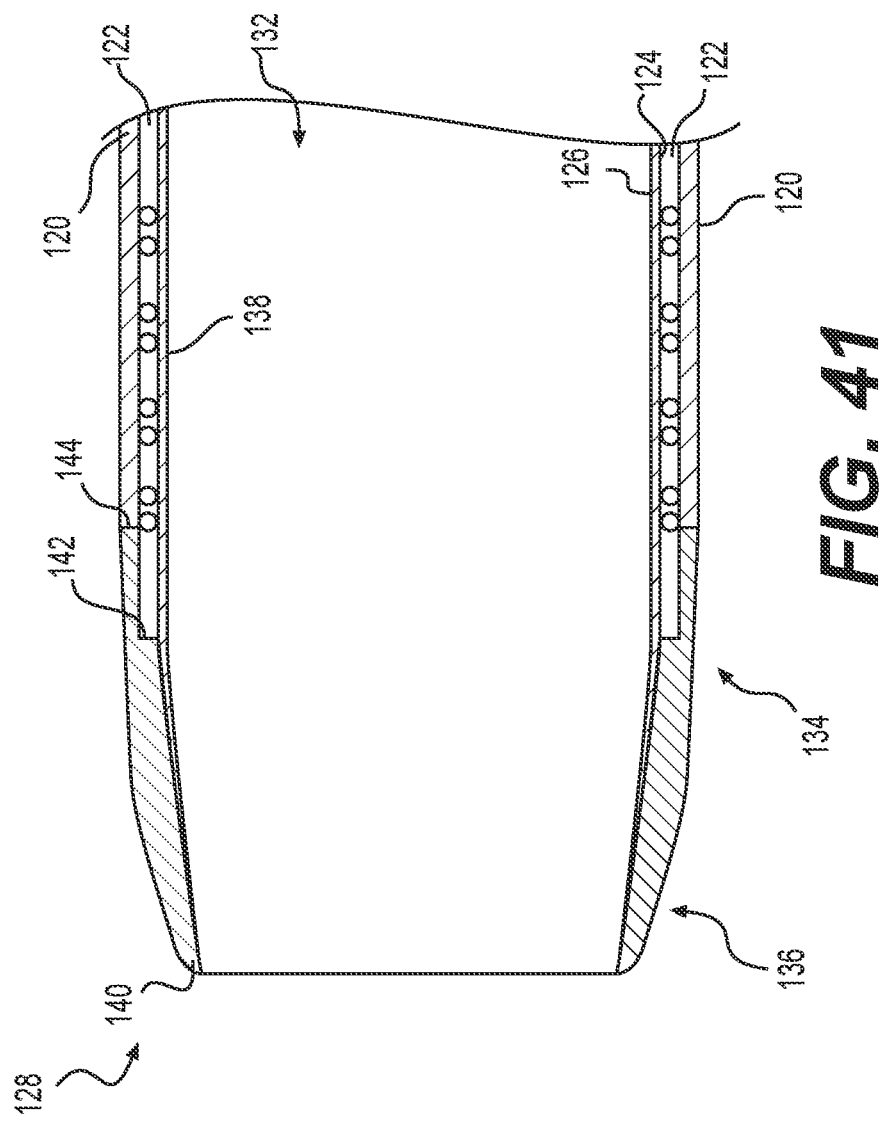
FIG. 41 is an enlarged view of a distal end of the sheath of FIG. 39.

As shown in FIG. 41, the distal tip 128, which has a tapering cylindrical construction, has a proximal taper 134, a distal taper 136, an inner surface 138 and a rounded leading edge 140. The proximal taper 134 has a relatively slight angle with respect to the parallel outer walls of the outer elastic layer 120. Generally, the tip has an outside diameter of about 0.25 inches at the distal end of the proximal taper and an outside diameter of about 0.26 inches at the proximal end of the proximal taper 134. The distal taper 136 has a higher angle increasing to about 20 degrees. The distal taper 136 has a length of approximately 0.060 inches. The leading edge 140 has a rounded radius of about 0.01 inches. The outermost diameter of the leading edge is 0.206 inches and the inner most diameter of 0.187 inches.

The inner surface 138 supports a progressively thinning, distally tapering portion of the mixed expandable layer 124 and inner lubricious layer 126—with the layers getting thinner in the distal direction. Together the inner surface and distally tapering portion of the layers 124, 126 define a distal portion of the lumen 132 through which the implant 105 and capsule 113 can exit.

At its proximal end the distal tip 128 includes an inner annular surface 142 and an outer annular surface 144. The inner annular surface is recessed within the proximal end of the distal tip 128 and the outer annular surface is on the proximal-most edge of the distal tip 128. The inner annular surface 142 is configured to receive and abut a distal edge of the mesh layer 122 and the outer annular surface 144 is configured to abut the distal edge of the outer elastic layer 120.

When assembled to the distal end of the layers 120, 122, 124 and 126 the distal tip 128—which is constructed of a relatively smooth, rigid material—provides support for advancement of the distal end of the sheath 103. The tapers and rounded outer edges minimize trauma when advancing through body lumens. Also, the distal tip 128 helps to maintain the end diameter of the sheath 103 after passage of the implant 105 and capsule 113.

The outer layer 120 has a tubular shape and is preferably constructed of a soft elastomeric material, such as a PEBAX or polyether block amide material, so as to easily expand in response to forces and return to its original dimensions. Also, the elastomeric properties urge the more inner layers to contract back to their original shapes. The outer layer can have an outer diameter of 0.260 inches and is the largest diameter of the layers making up the sheath 103. The outer layer 120 extends around and laminated onto the mesh layer 122 extending through its lumen.

Figure 40:
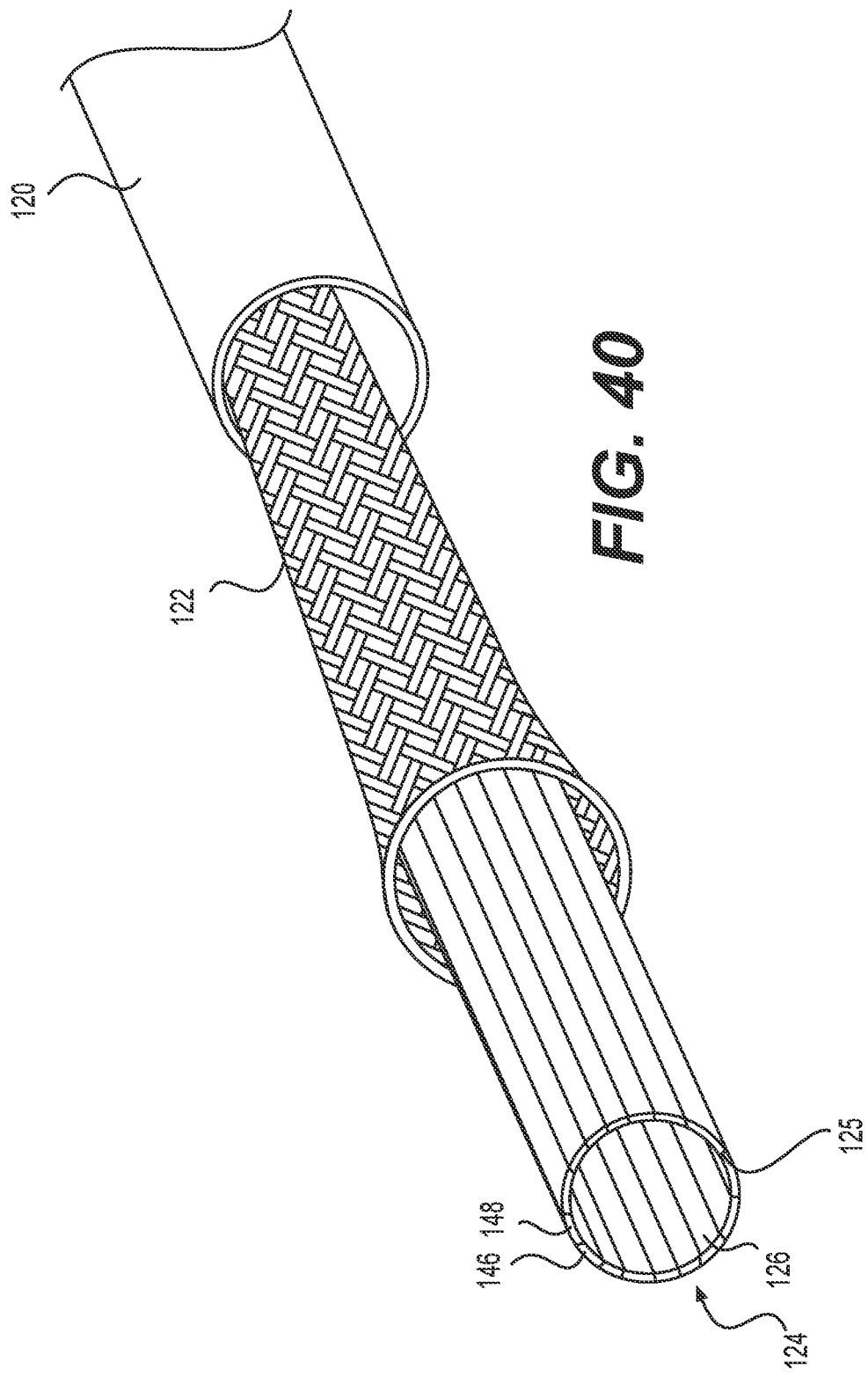
FIG. 40 is a partial exploded view of the sheath of FIG. 39.

The mesh layer 122 is preferably formed of a textile that is comprised of less-elastic components that obtain flexibility and some push stiffness from woven or knit construction. For example, the mesh layer can be constructed of a PET (polyethylene terephthalate) rope or thread material that is woven into a flexible mesh or a sleeve or tube with porous openings to promote expansion and flexibility. The mesh layer 122 can be formed as a plurality of braided fibers. FIG. 40, for example, shows the tubular shape of one embodiment of the mesh layer 122 wherein one group of threads extends perpendicular to another group of threads. Wires or metal could also be used to construct the mesh layer 122, such as woven superelastic nitinol wires with high elastic strain limits.

Figure 42:
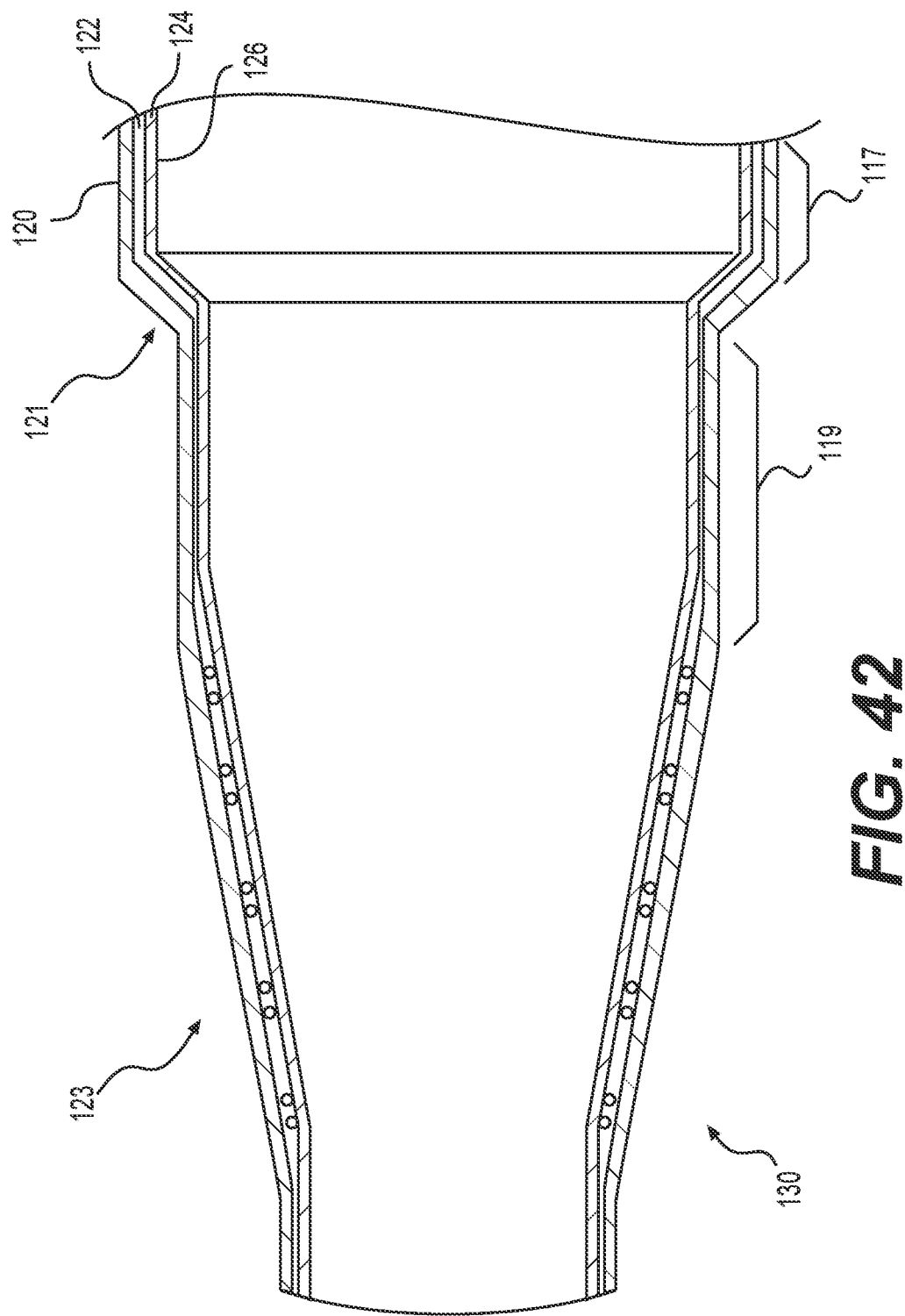
FIG. 42 is an enlarged view of a proximal end of the sheath of FIG. 39.

FIG. 42 shows a cross section of the flared proximal end of sheath 103. Like the distal end, the proximal end includes an outer elastic layer 120, a middle mesh layer 122, a mixed expandable layer 124 and an inner lubricious liner or layer 126. The most proximal region has a first annular portion 117 that is wider than the remainder of sheath 103. The layers 120, 122, 124, and 126 narrow sharply moving distally from the first annular portion of the proximal end 130, forming shoulder 121. The shoulder 121 and first annular portion 117 are configured to connect to the hub 104 of the delivery system 101. Moving distally from the shoulder 121, the layers extend distally to form a second annular portion 119. The walls of the first and second annular portions 117, 119 extend substantially parallel to the longitudinal axis 102 of the sheath 103, and the second annular portion 119 extends a greater distance than the first annular portion 117. Moving distally from the second annular portion 119, the layers 120, 122, 124, and 126 narrow again to form a taper 123. Taper 123 makes a smaller angle with the longitudinal axis 102 than shoulder 121. Taper 123 also extends a greater distance along the longitudinal axis 102 than shoulder 121.

Referring again to FIG. 40, the mixed, expandable layer 124 is constructed of a mixture of alternating full-thickness portions, including soft portions 146 and hard portions 148. The soft portions 146 are constructed of elastomer material—such as materials similar to the outer layer 120—that provide elasticity to the expandable layer 124. The hard portions 148 are constructed of a relatively stiff material and thus provide some columnar stability for advancing the sheath 103 against resistance of a body lumen. The number and spacing of the portions 146, 148 can be adjusted per application. Greater amounts or dimensions of stiff portions 148 can be included for more stiffness. Greater number or dimensions of soft/elastomeric portions 146 can be included for improved expandability and flexibility. TECOFLEX, an aliphatic polyether polyurethane, is one material that can be used for the stiff portions 148.

The portions have a radial thickness from the inside to outside diameter that is equal about the circumference of the layer 124. Also, each of the portions includes a pair of edges 125 between the hard and soft portions that extend between the inner and outer surfaces of the layer 124. The pair of edges can also extend longitudinally, in parallel to the long axis of the sheath 103. The soft/elastomeric portions 146 alternate with the hard portions 148 in arc-segments, their edges in abutting attachment, to form the tubular structure (with a consistent or constant wall thickness) of the mixed expandable layer 124. The hard and soft arc-segments can be equally sized, or they can vary in size as shown in FIG. 40.

The inner lubricious layer 126 coats or is adhered on inside surfaces of the expandable layer 124. The layer 126 is preferably a low-friction layer (such as PTFE) and can include a tie-layer attaching the lubricious material to the expandable layer 124. Advantageously, the composite of three layers—including an elastic outer layer, mesh layer and alternating hard/elastomeric layer and inner lubricious liner can provide a good balance of stiffness, expansion/recovery and low resistance to passage of implants.

FIG. 43A shows the delivery sheath 103 of another embodiment of the present invention with the capsule 113 carrying a stent-mounted heart valve or other prosthetic implant 105 passing through the sheath's lumen 132. (For example, the implant can be a 29 mm stent-mounted prosthetic heart valve.) The capsule 113 is passing in a proximal to distal direction. As used herein, "distal" (marked "D" in FIG. 43A), means towards the implantation site, and "proximal" (marked "P" in FIG. 43A) means away from the implantation site. The delivery sheath 103 is comprised of a transparent or semi-transparent material through which can be seen the capsule 113. Generally, the sheath of FIGS. 43A and 43B exhibits the ability to temporarily expand for passage of an oversized implant 105 and then return back to its normal diameter afterwards. Also, the sheath 103 can include multiple rods 150, that can be seen through the sheath, and that facilitate lower friction passage of the capsule 113.

FIG. 43B shows a cross section of the delivery sheath 103 including a stiff wall portion 152, an elastic wall portion 154 and the rods 150. The stiff wall portion 152 has a partial circular, or arc-shaped, or C-shaped cross-section with a consistent wall thickness within the cross-section. The C-shape of the stiff wall portion has a pair of edges 156 that extend between the inner and outer surfaces of the stiff wall portion 152. Perpendicular to the cross-section, the two edges extend generally along the length of the stiff wall portion 152 and in the direction of, and parallel to, the elongate axis of the delivery sheath 103.

The elastic wall portion 154 extends between the free edges 156 of the stiff wall portion 152 to define an expandable tubular layer and close the lumen 132 of the sheath 103. As shown in FIG. 43B, the elastic wall portion generally has a shorter arc-length than the stiff wall portion 152 and is positioned further away radially from the axis of the sheath 103 than the inside surface of the stiff wall portion 152. This additional radial clearance provides room for the three rods 150 to extend into the lumen 132. The elastic wall portion 154 can comprise an angle 158 of at least 20 degrees, or as much as 45 to 90 degrees of the cross-section of the sheath 103. The combination and proportions of the elastic and stiff wall portions 154, 152 provide for the temporary expansion and return of the lumen diameter 132 during passage of the implant 105.

The elastic wall portion 154 can be part of an outer elastic tubular layer 162 that externally encapsulates the stiff wall portion 152 in a seamless elastomeric layer. In this manner, the elastic tubular layer 162 helps to seal off the lumen 132 and to urge the C-shaped stiff wall portion 152 back to its original diameter when no longer under pressure from a passing implant. Although the sheath of FIGS. 43A and 43B can have a range of dimensions to suit different applications, the stiff wall portion 152 can, for prosthetic valve delivery purposes, range from 0.002 inches to 0.020 inches in thickness, including about 0.015 inches. The outer portion of the elastic tubular layer 162 adds about another 0.002 inches to 0.020 inches, and in particular about 0.005 inches. In one application, then, the total thickness of the sheath 103 wall can be about 0.020 inches. The unexpanded lumen 132 can have a diameter from 0.050 to 0.250 inches, such as 0.156 inches.

FIG. 43B shows three of the rods 150 embedded into the elastic wall portion 154 and extending into the lumen 132 of the sheath 103. The rods 150 are elongate structures with extruded cross sections—such as a cylindrical shape with a circular cross-section—that extend along the longitudinal axis of the sheath 103. The rods 150 of FIG. 43B are equally spaced from each other in a circumferential direction between the edges 156 of the C-shaped stiff wall portion 152. Advantageously, the spacing of the rods 150 can increase, as shown in FIG. 43A, during passage of the capsule 113 with stretching of the elastic wall portion 154.

Thus the rods can provide some additional stiffness and reduce the surface area and friction that would otherwise be present between the elastic wall portion and the passing implant or capsule without much impact on the expandability of the sheath. As can be seen, at least about half of the cross-section of the rods 150 extends into the lumen 132.

The C-shaped stiff wall portion 152 can be comprised of a range of stiff materials, such as a high-density polyethylene or nylon which provides buckle resistance, pushability, torqueability and a relatively stiff body for the sheath 103. The combination of the elastomeric soft portion 146 helps to mediate kinks of the sheath and to bias against the opening tendency of the stiff wall portion 152. A proximal end of the expandable tubular layer including the wall portions 152, 154 and the outer elastic tubular layer 162 can be flared to provide for hub attachment. Also, a tip could be constructed from the same elastomeric material as the wall portion 154. The tip could include radiopaque properties and be heat fused to the outer tubular layer 162. Manufacture is fairly easy since the components of the sheath 3 can be co-extruded in a single operation.

Figure 44:
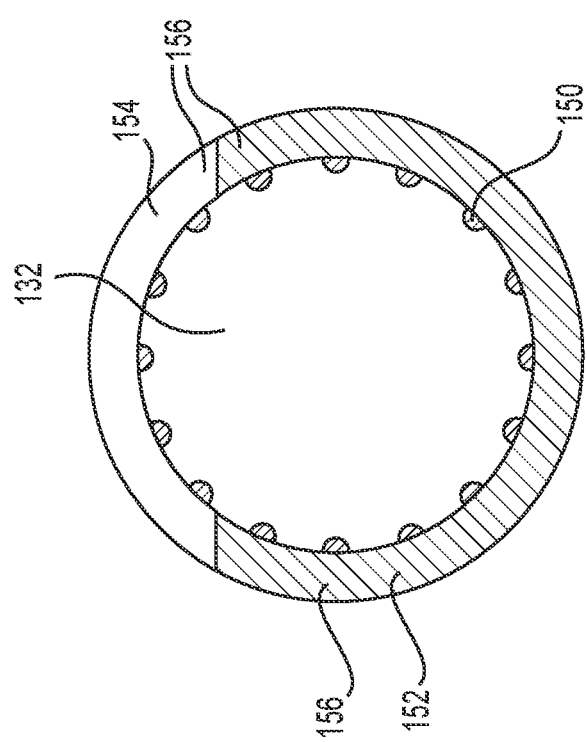
FIG. 44 is a cross sectional view of a sheath of another embodiment.

FIG. 44 shows another embodiment of sheath 103 including wall portions 152, 154 and rods 150 similar to the sheath 103 in FIGS. 43A and 43B. In this embodiment, however, the edges 156 of the stiff wall portion 152 are oriented to be within a common plane. The elastic wall portion 154 also has a thickness matched to the stiff wall portion 152, as opposed to having the encapsulating outer elastic tubular layer 162. The elastic wall portion 154 also takes up a larger angle 158 than the embodiment shown in FIGS. 43A and 43B.

The sheath 103 also includes a larger number of rods 150 which are equally spaced circumferentially about the entire lumen 132. The rods 150 are connected to the inside surfaces of both the stiff wall portion 152 and the elastic wall portion 154. The rods 150 have a semi-circular extruded cross-section. The additional rods 150 can further reduce contact area and the associated friction. The rods 150 can be comprised of stiff, relatively lubricious material to further facilitate sliding. The rods 150 on the stiff wall portion 152 can allow reduction of the overall stiffness of the wall portion as the rods 150 help to increase stiffness.

FIGS. 45A-45D show embodiments wherein the sheath 103 includes an elastic tubular layer 166 having covering one or more stiff wall portions 168. The elastic tubular layer 166 can be a seamless outer layer that guards against blood or fluid leakage. The stiff wall portions define one or more gaps 170. Generally, the cumulative circumferential amount of the cross-section taken up by the gaps 170 is proportional to the resistance to expansion of the sheath 103 at that particular longitudinal position. FIGS. 45A-45D, for example, show the cumulative amount of the gaps 170 increasing distally so that the amount of compression exerted on the implant drops in the distal direction. This can be advantageous as the friction and/or other resistance to advancement of the capsule 113 within the sheath can increase with increase in distance of travel—the drop in expansion resistance can offset somewhat the increased push resistance.

Figure 45B:
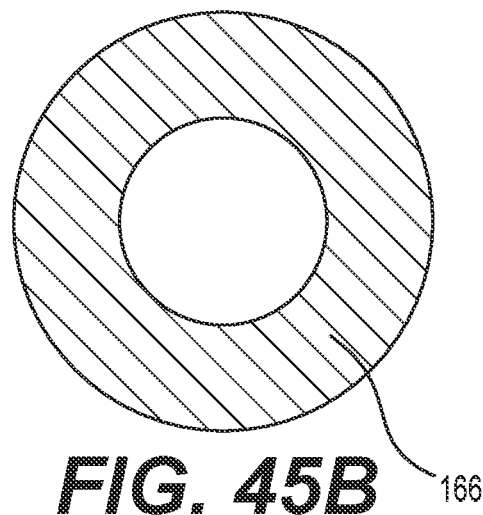
FIGS. 45B-45D are cross sectional schematics of the delivery sheath implementation shown in FIG. 45A.
Figure 45C:
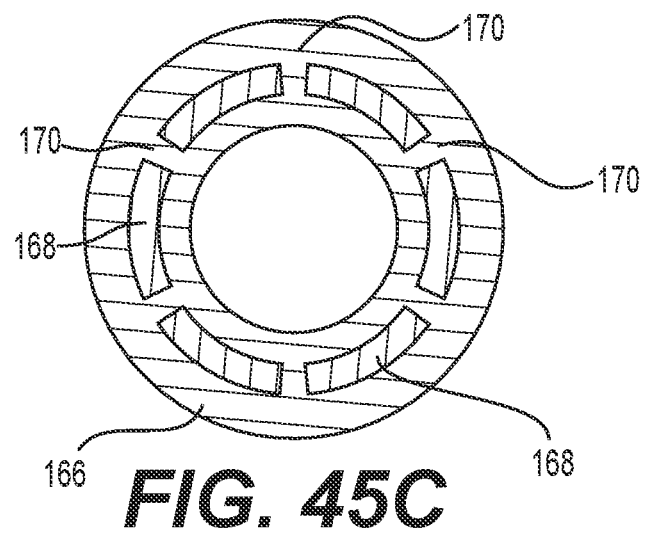
Figure 45D:
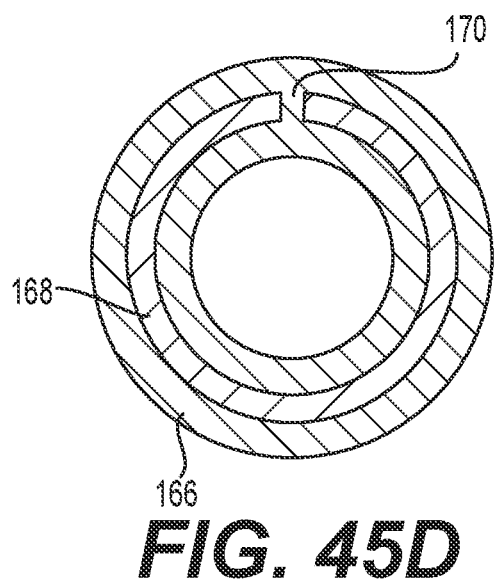

The cross-section shown in FIG. 45D, for example, is taken from a more proximal position and the embedded stiff wall portion 168 takes up significantly more than half of the circumference of the sheath 103. The single gap 170 between ends of the stiff wall portion 168 is about 45 degrees of the circumference forming a C-shaped tube similar to the stiff wall portion 152 described above. Moving distally to the cross-section shown in FIG. 45C shows an additional set of four smaller gaps 170 added to the larger gap. These gaps, as shown in FIG. 45A, tend to define the stiff wall portion 168 into discrete fingers 174. With the increase of the gap size in proportion to the size of the stiff wall portion 168, the expansion stiffness of the sheath 103 drops. The cross-section shown in FIG. 45B is at the distal end and now the stiff wall portion 168 is not present, substantially increasing the expandability of the distal end of the sheath 103.

The gaps 170 can have a range of sizes and positioning, although the gaps shown in FIGS. 45A-45D extend longitudinally and generally parallel to each other. The smaller gaps are circumferentially arranged and spaced from each other and from the larger gap. The multiple gaps 170 with regular spacing facilitate even expansion of elastic tubular layer 166. The full axial length gap can also be of similar circumferential size as the other gaps 170 for a more even distribution of expansion. For example, for six gaps, a 300% strain of a C-shaped tube is divided into 50% at each location. In contrast, tips with a single gap have more localized expansion of the layer 166 and some risk of fracture.

It should be noted that the term 'axial' as used herein is not limited to a straight axis but instead is referring to the general instantaneous direction of a longitudinal structure. In other words, the axis bends with a bend of the elongate structure.

Figure 46B:
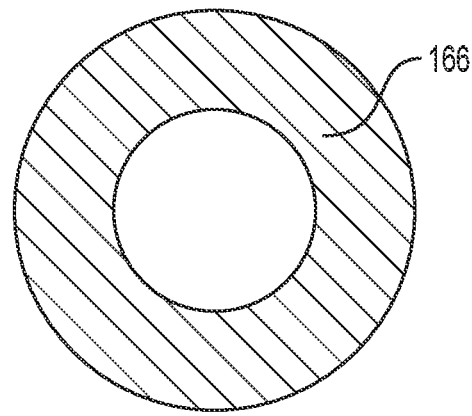
FIGS. 46B-46D are cross sectional schematics of the delivery sheath implementation shown in FIG. 46A.
Figure 46C:
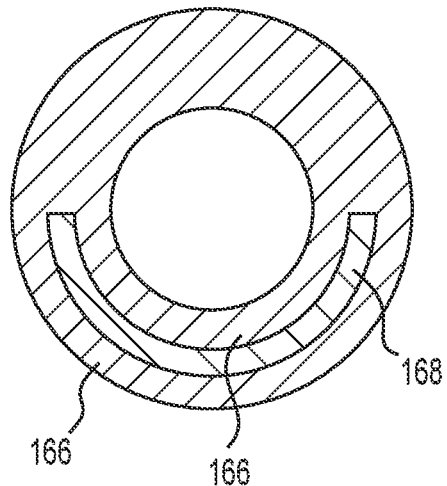
Figure 46D:
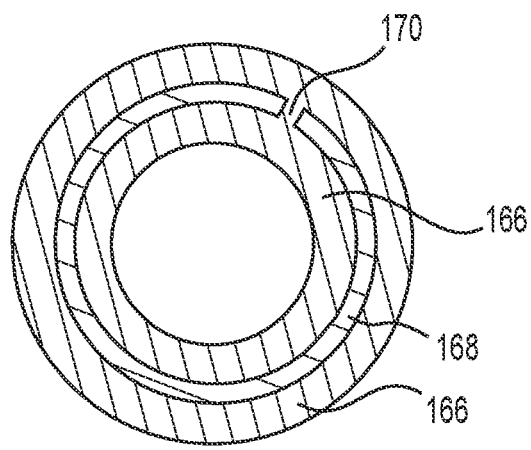
Figure 47B:
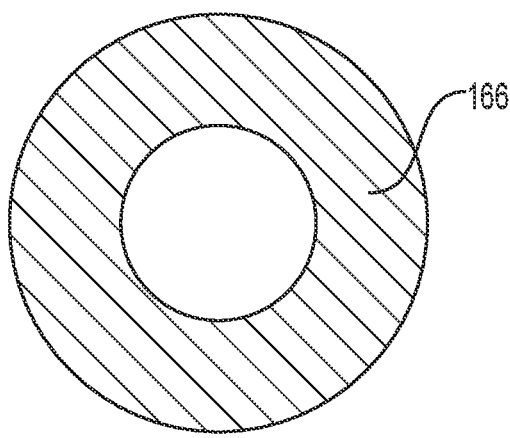
FIGS. 47B-47D are cross sectional schematics of the delivery sheath implementation shown in FIG. 47A.
Figure 47C:
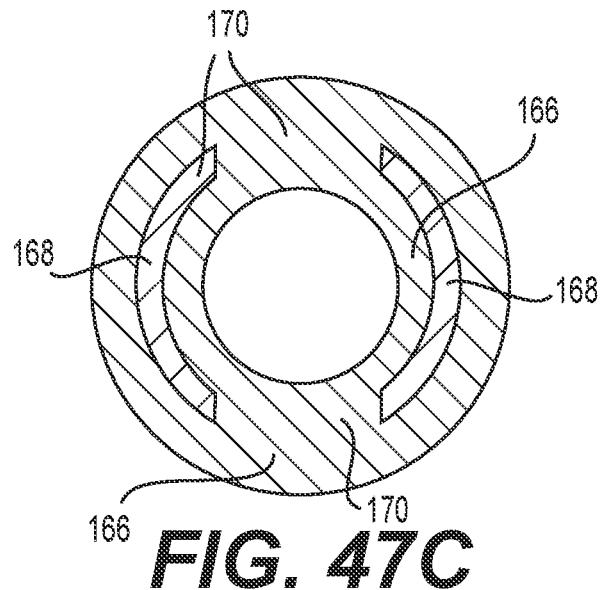
Figure 47D:
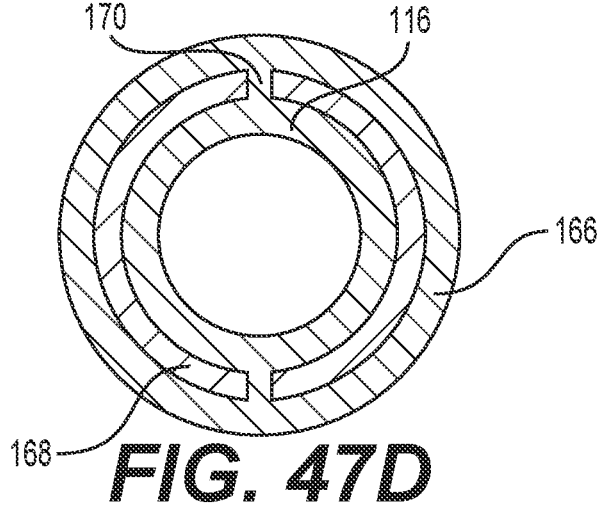
Figure 48A:
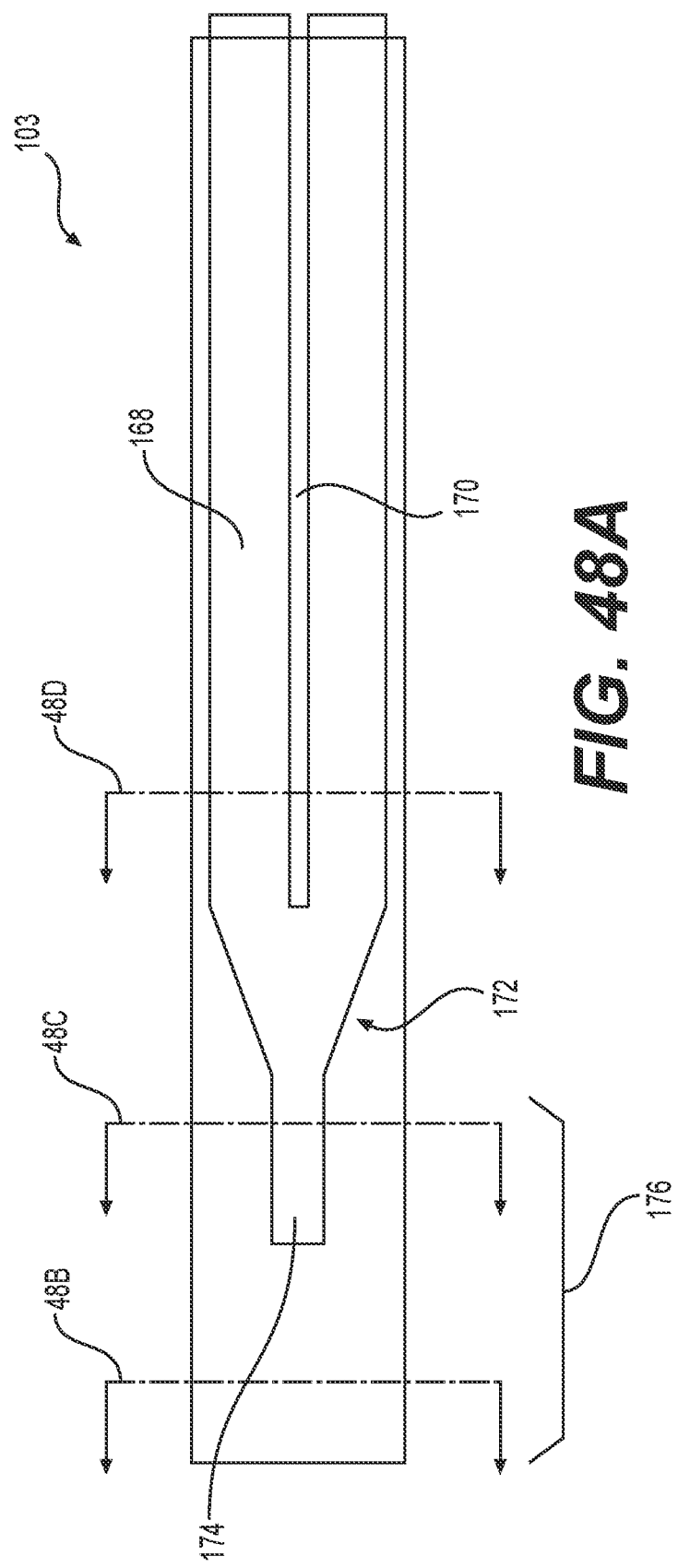
FIG. 48A is a schematic of another implementation of a delivery sheath with increasing elasticity approaching the distal end region.
Figure 48B:
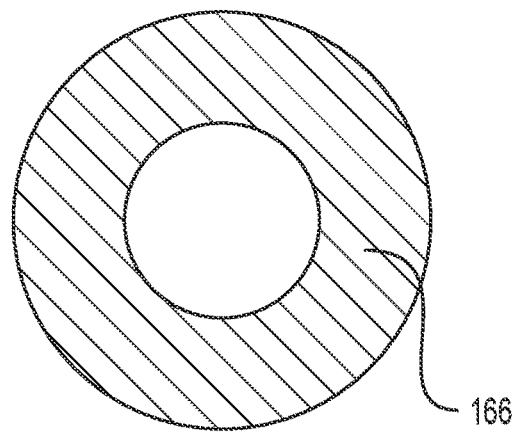
FIGS. 48B-48D are cross sectional schematics of the delivery sheath implementation shown in FIG. 48A.
Figure 48C:
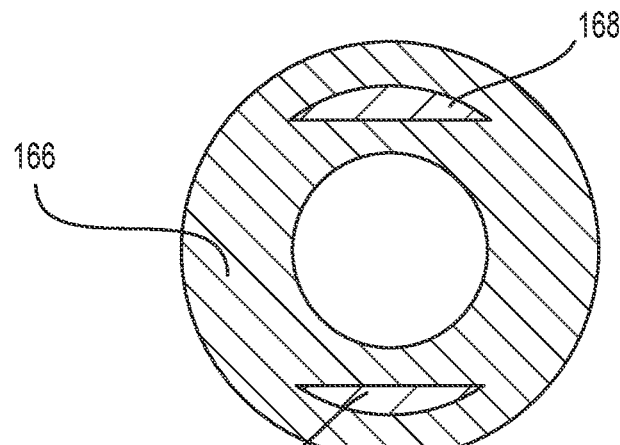
Figure 48D:
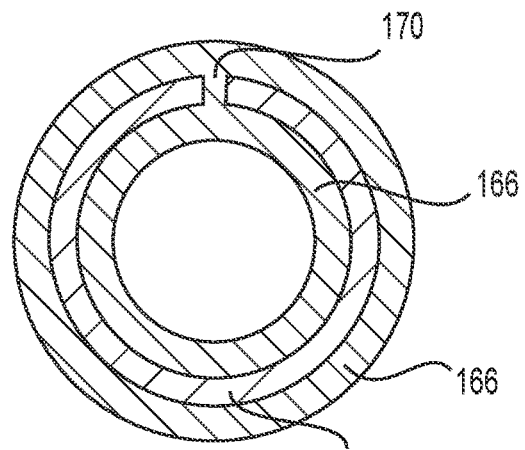
Figure 49B:
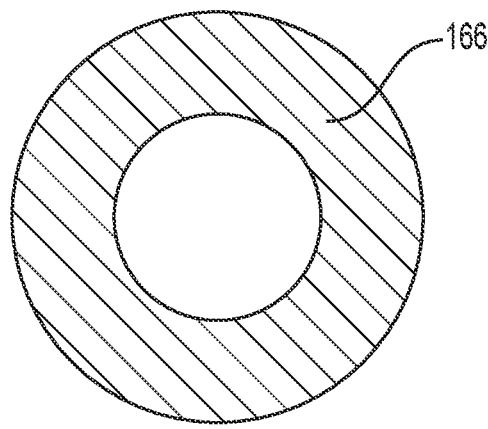
FIGS. 49B-49D are cross sectional schematics of the delivery sheath implementation shown in FIG. 49A.
Figure 49C:
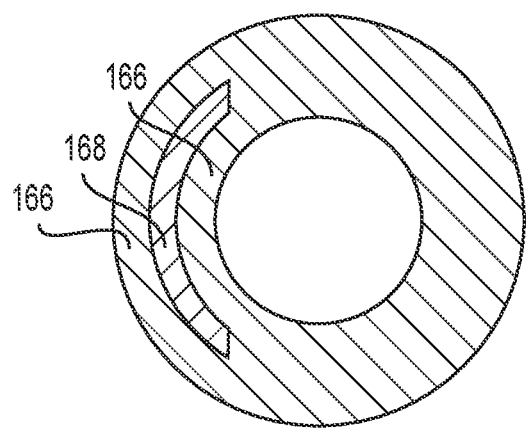
Figure 49D:
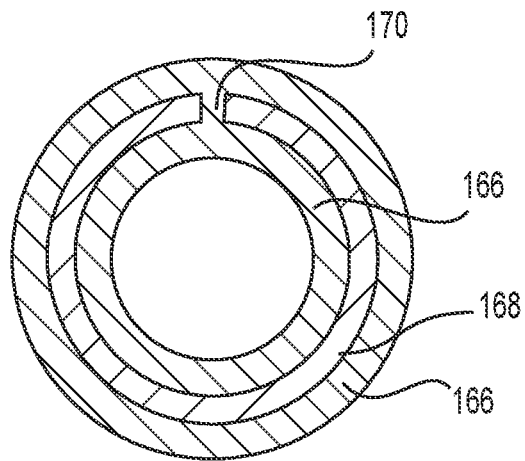

FIGS. 46A-46D show another embodiment wherein the sheath 103 has a single one of the gaps 170 extending longitudinally and then a diagonal cut forming a distal-facing diagonal surface. The diagonal cut serves to progressively decrease the amount of cross-section occupied by the stiff wall portion 168 as it extends in the distal direction, as shown by FIGS. 46D, 46C and 46B.

FIGS. 47A-47D show another embodiment wherein the sheath includes a pair of gaps 170 on opposite sides of the stiff wall portion. The pair of gaps expand in the distal direction, being smallest in diameter at the proximal cross-section of FIG. 47D, making a step increase in size to the cross-section of FIG. 47C. At the final transition, the stiff wall portion 168 disappears for cross-section FIG. 47B. This pattern provides a step decrease in resistance to expansion with each transition in the distal direction.

FIGS. 48A-48D show another embodiment wherein one of the gaps 170 disappears when the stiff wall portion starts a pair of converging diagonal surfaces 172. The diagonal surfaces converge to a single pair of opposing fingers 174. Again, the change in proportion of circumference occupied by the stiff wall portion 168 and gaps 170 adjusts the resistance to expansion of the distal end of the sheath 103.

FIGS. 49A-49D show a combination of some of the prior concepts, wherein the sheath 103 includes the diagonal surface 172 converging to one finger 174.

In the embodiments of FIGS. 45A-49D, the elastic tubular layer 166 and stiff wall portion can move independently of one another for freer expansion. This can be supplemented with addition of a tip region 176, such as by reflowing a soft expandable tube or coating over the distal end of the cuts defining the gaps 170 in the C-shaped stiff wall portion 168. Adding the tip can soften and contour the tip for easier insertion of the sheath 103 as well as protect and cover the distal end of the stiff wall portion 168. In FIGS. 45A-45D the tip region 176 covers some or all of the longitudinal length of the fingers 174 while the remainder of the stiff wall portion with only the single C-shaped cross-section (e.g., FIG. 45D cross-section) is left independent of the elastic tubular layer 166 for free expansion. In FIGS. 46A-49D, the tip region can start distal of the termination of the single gap defining the C-shaped cross section of FIG. 46D.

Although embodiments of the sheath 103 disclosed herein have particular layer constructions, they can include additional layers extending around the inside or outside of the layers depicted in the figures. For example, in some implementations, an undercut/bard or tie layer can be included to keep the stiff wall portion 168 attached to the elastic tubular layer 166. In some implementations, a lubricious outermost layer can be included. The lubricious outermost layer can include a slip additive to increase outer surface lubricity.

In some implementations, such as the one shown in FIG. 43B, the first and second layer 154, 162 and wall portion 152 (which is another layer) are bound together, for example, due to fabrication methods that include coextrusion, heat bonding, glue, or another fixative material. Coextruded implementations are particularly advantageous as they are simple and inexpensive to manufacture. Coextrusion also reduces delamination of outer circumferential layers from inner circumferential layers. In other implementations, the layers are not fully bound and are at least partially, and possibly fully, rotatable with respect to each other. For rotatable implementations, the circumferential tension experienced when an implant 105 is passing through is distributed around the layers 120, 154 and 166, instead of being localized to particular locations. This reduces the chance of rupturing those outer layers. In some implementations, the layers are bound together over certain lengths of the sheath 103, and rotatable over other lengths of the sheath 103. In some implementations, the first and second circumferential layers are bound together only at the distal end region of the sheath 103. Selectively allowing rotation of some portions of the layers allows for some improved tear resistance while preserving some element of structural stiffness. In some implementations, the proximal end of sheath 3 can be flared to attach to external components of the sheath.

In some implementations, various portions of the illustrated embodiments can be supplemented with the longitudinal rods 150. The rods can extend, either partially or fully, along the length of the inner-most surface defining the lumen 132 of the sheath. The longitudinally extending rods can, for example, be supported by the inner-most surface. Here the term "supported by" can mean that the rod is in contact with or extends through that inner surface. For example, the rod can be adhered to or formed on the inner most surface. In some implementations, the longitudinally extending rods can be fully embedded within the inner-most layer. In other implementations, longitudinally extending rods 150 can be partially embedded within the layer, and partially protruding into the inner lumen of the sheath, such as is shown in FIG. 43B.

The height and width of the longitudinally extending rods 150, and thus the amount of the sheath cross-section devoted to the non-elastomeric portions, can vary along the length of sheath 103. A width 143 of the longitudinally extending rods 150 can be, for example, from 0.001 to 0.05 inches. The rods 150 can be circular, ellipsoidal, polygonal, rectangular, square, or a combination of parts of the afore-listed shapes when viewed from a cross section taken generally perpendicular to an elongate axis 102 of the sheath 103. Rods 150 with curved surfaces that protrude into the lumen, such as circular or ellipsoidal surfaces, have the advantage of reducing the area of contact, and therefore the friction, between the sheath and a passing object. Longitudinally extending rods also minimize dimensional change in the longitudinal direction when the sheath is under tension.

Components described as elastic herein can be constructed of elastomers, such as a highly elastic polymer. In some implementations, the elastomeric portion can include polyether, polyurethane, silicone, thermoplastic elastomers, rubber such as styrene-butadiene rubber, or a copolymer of any of the afore-listed highly elastic polymers. The elastomeric material can have an elongation of around 800%. In some implementations, the elastomeric components can comprise a NEUSOFT polymer. The hardness of the NEUSOFT polymer can be, for example, 63 Shore A. NEUSOFT is a translucent polyether urethane based material with good elasticity, vibration dampening, abrasion and tear resistance. The polyurethanes are chemically resistant to hydrolysis and suitable for overmolding on polyolefins, ABS, PC, Pebax and nylon. The polyuerthane provides a good moisture and oxygen barrier as well as UV stability.

The heightened elasticity of various elastic layers, such as layers 120, 162 and 166, facilitates expansion of the layer from its starting profile to allow for the passage of a prosthetic implant 105 and/or delivery capsule 113. In some implementations, an in particular for passage of a capsule containing a stent-mounted prosthetic implant, the lumen can expand to 0.15-0.4 inches, in a fully expanded state. For example, in one implementation, the original diameter of the lumen is 0.13 inches, expands to 0.34 inches during passage of an implant, and shrinks back to 0.26 inches immediately after passage of the implant and continues to shrink with time until eventually returning back to about 0.13 inches. After the passage of the implant, the lumen collapses back to a narrower diameter due to the elasticity of the elastomeric components.

The non-elastomeric components of embodiments described herein (sometimes particularly described as stiff) are made of a generally stiff material that is less elastic than the elastomeric components. The stiff components lend strength to the sheath 103 to complement the elastic properties contributed by the elastomeric components. The stiffer, non-elastomeric components also contribute to buckle resistance (resistance to failure under pressure), kink resistance (resistance to failure during bending), and torque (or ease of turning the sheath circumferentially within a vessel). The stiff material used to fabricate the stiff components can include high density polyethylene (HDPE), Nylon, polyethylene terephthalate (PET), fluoropolymers (such as polytetrafluoroethylene or PTFE), Polyoxymethylene (POM) or any other suitably stiff polymer. The elongation of the non-elastomeric, stiff components can be, for example, around 5%. The hardness of an HDPE non-elastomeric, stiff component can be, for example, around 70 Shore D.

The non-elastomeric components can also be made of a material that is more lubricious than the elastomeric components, and so as to reduce friction between components and/or the components and the implant 105, capsule 113 or other adjacent contacting objects.

Embodiments disclosed herein can be employed in combinations with each other to create sheaths with varying characteristics. FIG. 50 shows combination of two single-layer tubes nested into each other. Each of the single layer tubes includes a stiff wall portion 152 having a C-shape and an elastic wall portion 154 to close the C-shape around lumen 132. Each single layer tube also includes rods 150 in a similar configuration to the embodiment of FIG. 43B. One of the single layer tubes has a smaller diameter and fits within the lumen 132 of the other tube. The advantage of this combination is a more balanced distribution of elastic wall portions 154 on both sides of the tube which in turns distributes the strains of expansion. The other embodiments disclosed herein can be nested within each other to adjust expansion resistance and distribution.

Figure 51:
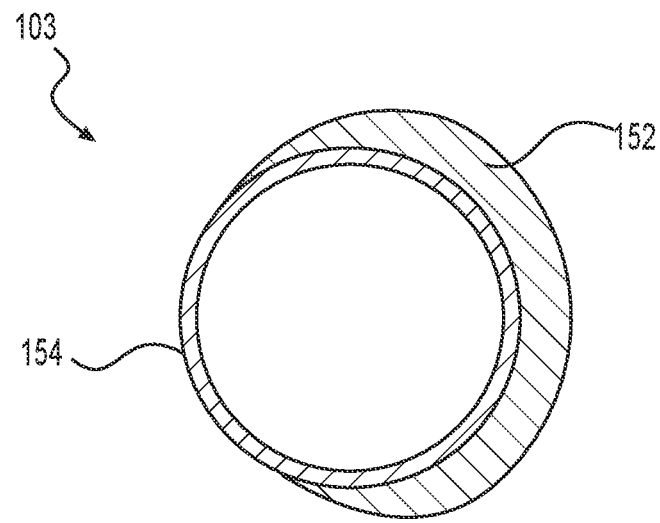
FIGS. 51-53 are cross-sections of embodiments sheaths having expandable thinned wall sections.
Figure 52:
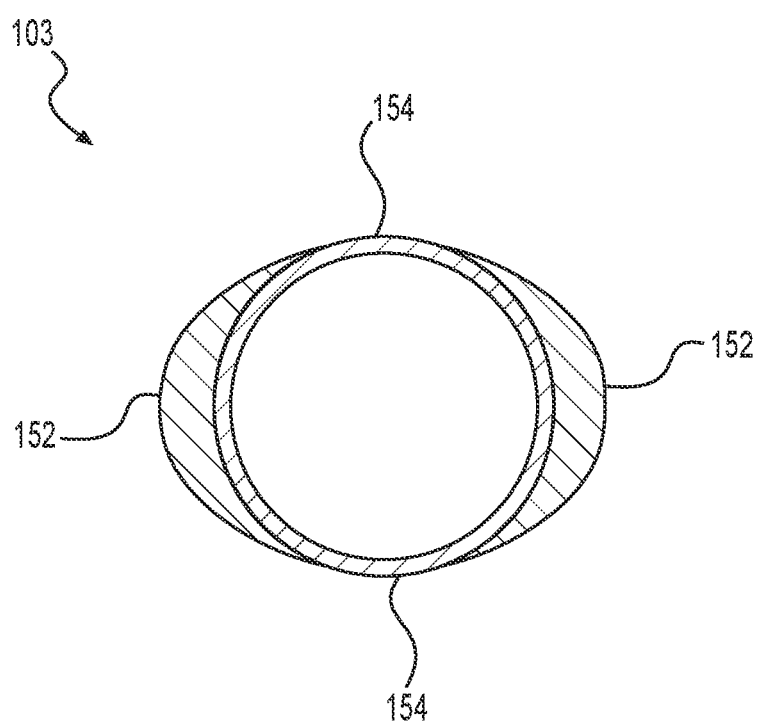
Figure 53:
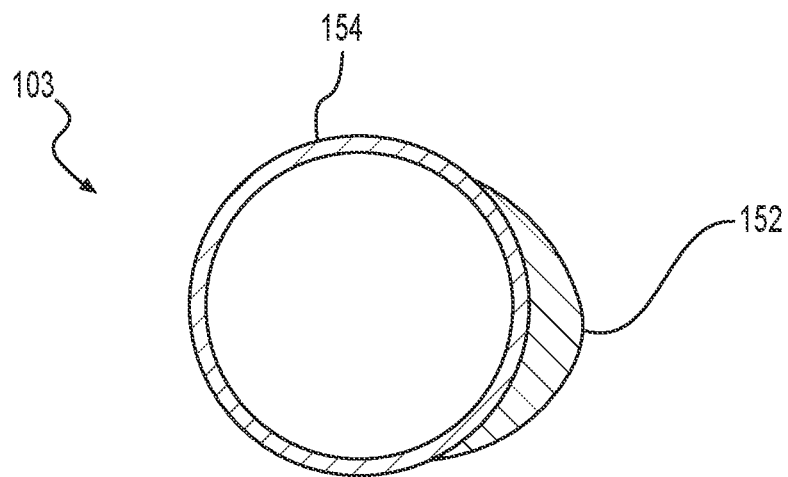

FIGS. 51, 52 and 53 show variations of the sheath 103 that include stiff wall portion 152 and elastic wall portion 154, with the elastic wall portion having a lesser wall thickness for additional flexibility in comparison with the stiff wall portion 152. In these embodiments the wall portions can have the same material with the additional flexibility being due to the reduced thickness. Or the reduced thickness can be combined with more elastomeric material composition.

FIG. 51 shows an embodiment of the sheath 103 with a C-shaped stiff wall portion 152 combined with a thin elastic wall portion 154. FIG. 52 shows the use of two elastic wall portions 154 and two thick, stiffer wall portions 152 on opposing sides, positioning the strain of expansion on opposing sides of the sheath 3. FIG. 53 shows an embodiment of the sheath 103 with more than half or ⅔ or ¾ of the circumference of the sheath being a thinned elastic wall portion 154.

Figure 54:
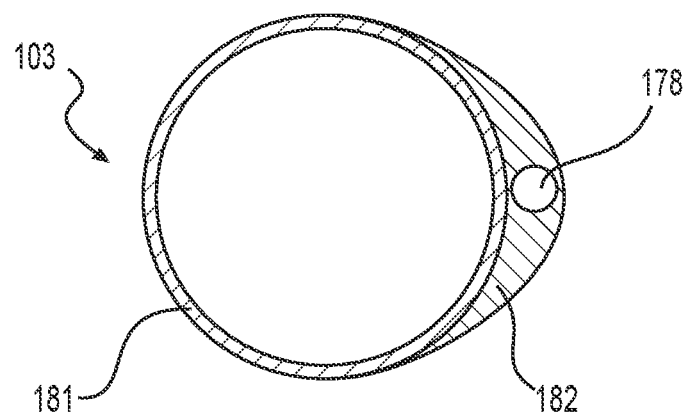
FIGS. 54-56 are cross-sections of embodiments of sheaths having wires or strips reinforcing expandable walled tubes.
Figure 55:
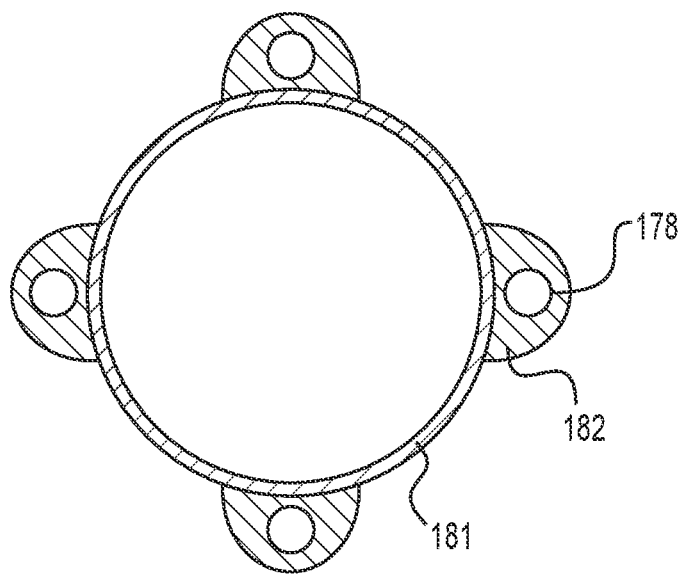
Figure 56:
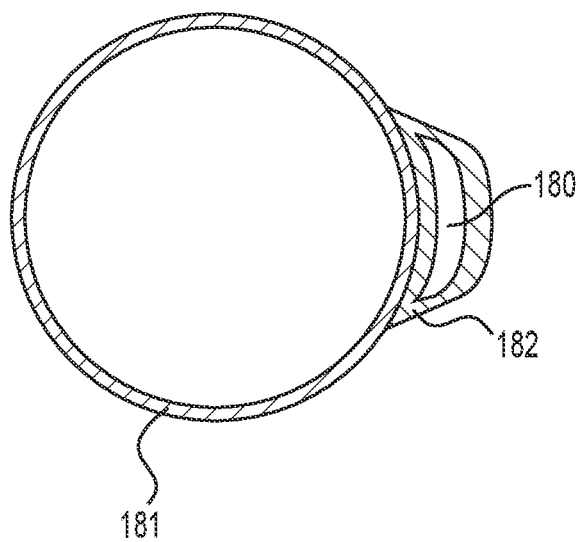

FIGS. 54, 55 and 56 show embodiments wherein wires 178 or strips 180 can be embedded into structures 182 to selectively reinforce an expandable, elastic tubular layer 181. The structures 182 can be thickened mounds or features applied longitudinally—such as be co-extrusion—to the outside surface of the elastic tubular layer 181. The wires or strips can be constructed of relatively stiffer materials for selective reinforcement. FIGS. 54 and 55 show the use of wires 178 and, for increased stiffness, FIG. 56 shows the use of a strip 180 embedded in the structure 182.

The sheaths of FIGS. 51-56 can be manufactured as described above, including via reflowing, gluing, bonding, welding, etc. Materials can include HDPE or TECOFLEX for the stiffer components. Other materials herein can also be used for stiff or elastic components. Also, the materials compositions can be varied to include metals, ceramics and other materials than just polymers. Other features can be applied to the embodiments of FIGS. 51-56 including a lubricious liner, hydrophilic or other coatings, silicone or other liquids or printing.

Figure 57:
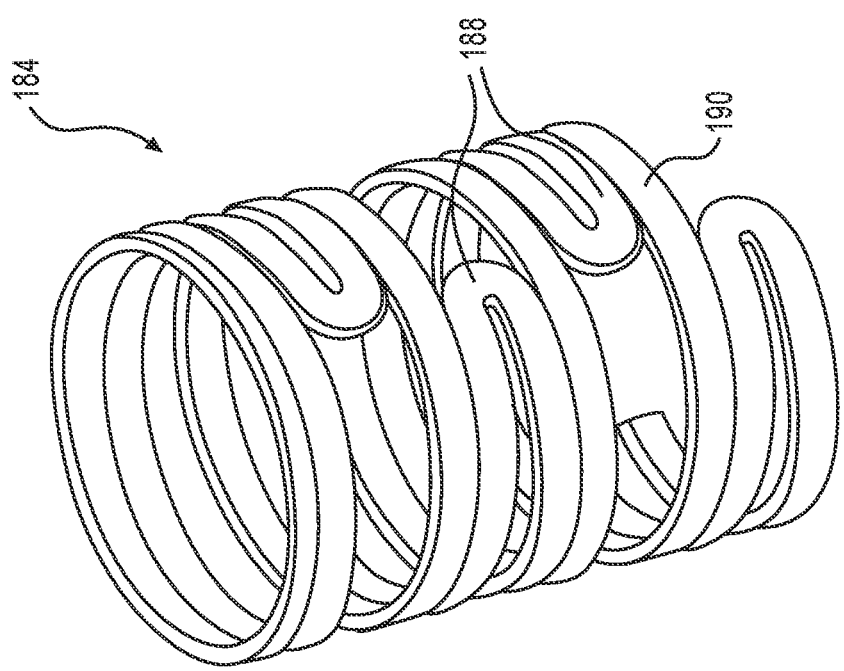
FIG. 57 is a partial perspective view of a stent for an end of a sheath of another embodiment of the present invention.
Figure 58:
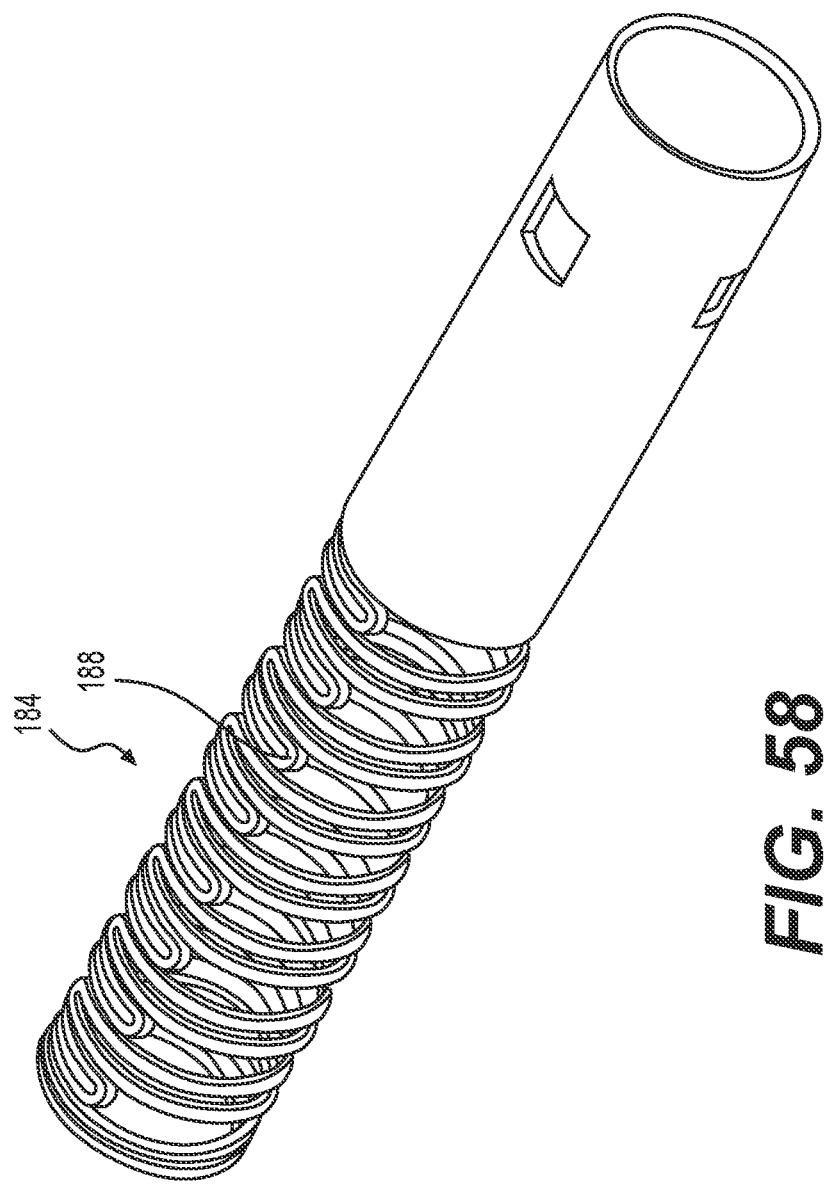
FIGS. 58-60 are perspective views of an embodiment of a stiff wall structure of a sheath having a distal stent portion progressively opening to increase its lumen diameter.
Figure 59:
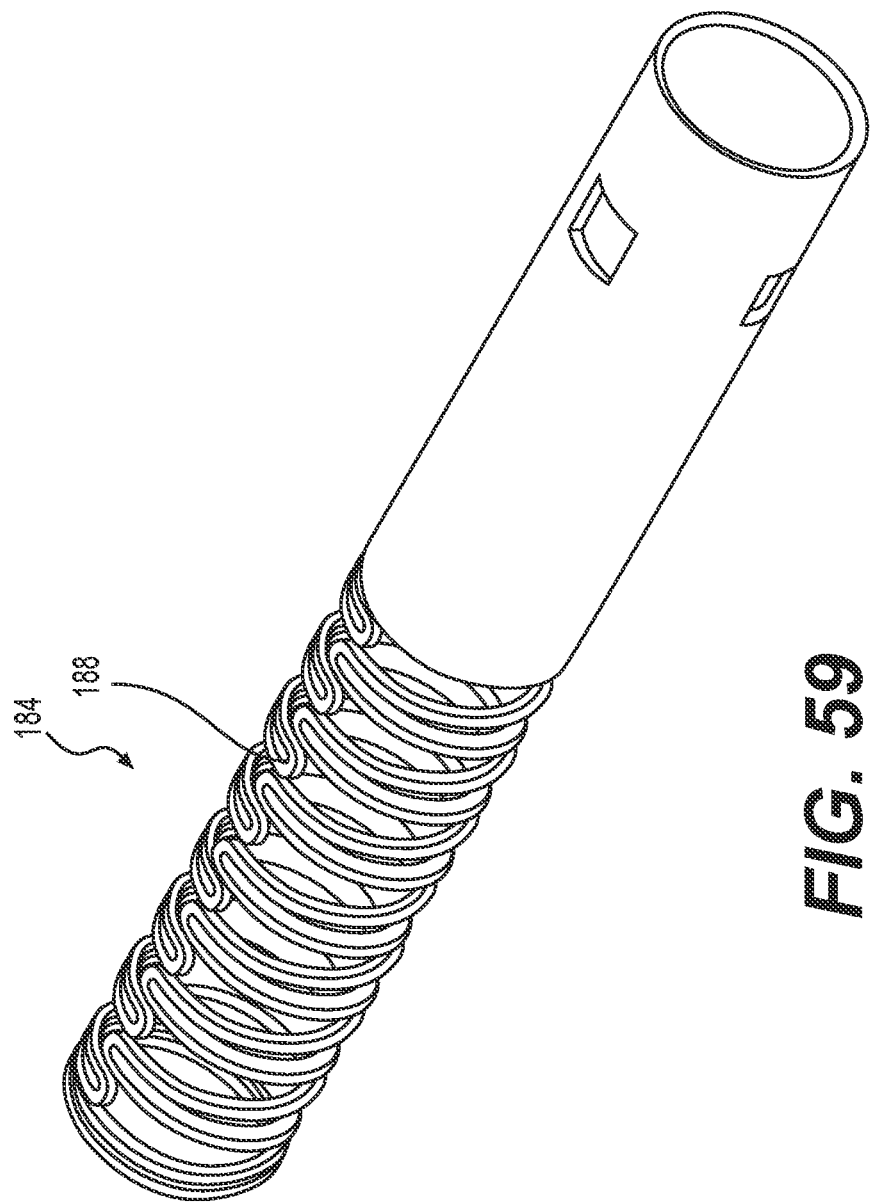
Figure 60:
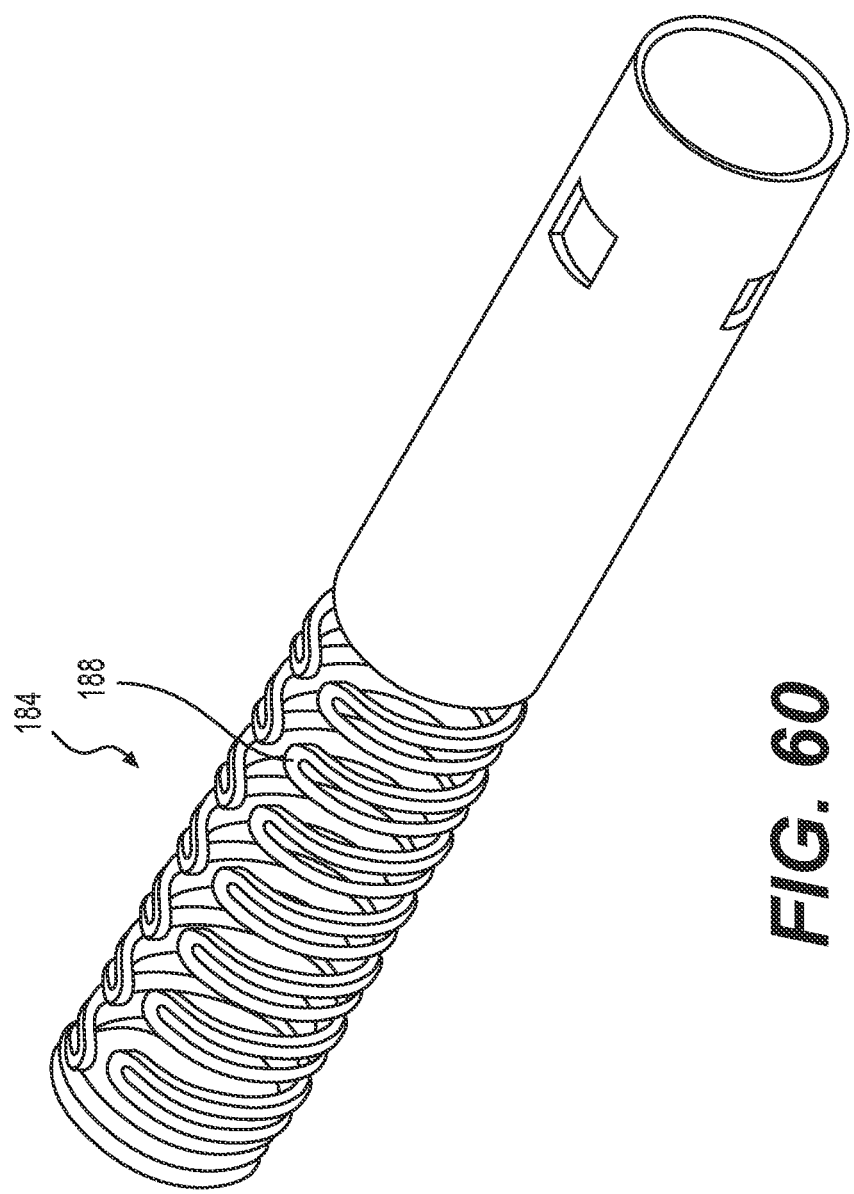

As shown in FIGS. 57-60, another embodiment of the sheath 103 can include a stent structure 184 for embedding in an elastic tubular layer. The stent 184 can include a plurality of loops 188 facing in opposite circumferential directions and that interdigitate between (FIGS. 58-60) or adjacent each other (FIG. 58) so as to be able to open up under pressure of the implant 105 passing therethrough. FIG. 57 shows an additional full circular winding 190 in between each of the loops 188 for additional stiffness. FIGS. 58, 59 and 60 show the progressive expansion of the lumen within the stent 184 as the implant 105 passes therethrough. The stent 184 can have varying lengths and in the illustrated embodiments is used for the distal end of the sheath 103. The stent 184 could also include a heat fused tip on its distal end as shown in other embodiments.

The stent 184 is a shaped frame that can be formed from a laser cut tube or by bending wire into the frame. Similar to the C-shaped stiff tubes, the stent 184 results in an off-center axial load during passage of the prosthetic implant 105. The adjacent relationship of the loops 188 and/or windings 190 provide for excellent pushing stiffness to resist buckling while still having circumferential/radial expandability. Thus, the sheath has a particularly high ratio of buckling to expansion force—allowing for good articulation with easy expansion. The stent 184 is also particularly suited for protecting delicate implants 105, like stent-mounted prosthetic heart valves. The stent 184 can be coated by polymers for hemostatic sealing and protection of the external structures of the prosthetic implant 105.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A sheath defining a central lumen and comprising:
multiple longitudinal segments;
an expandable inner layer extending along the multiple longitudinal segments and comprising multiple longitudinally extending folds, each longitudinally extending fold comprising portions of the expandable inner layer arranged in an overlapping configuration that move to a less overlapping configuration to allow passage of an implant therethrough, thereby increasing a diameter of a central lumen defined by the sheath, and
an outer tubular layer surrounding the expandable inner layer and extending along multiple longitudinal segments,
wherein a first longitudinal segment of the sheath comprises an interdigitating stiffening structure as part of the outer tubular layer, the interdigitating stiffening structure surrounding the expandable inner layer and comprising a plurality of protrusions facing in alternating circumferential directions and interdigitating between each other,
wherein the first longitudinal segment of the sheath is configured to temporarily expand to allow passage of an implant through the central lumen by at least partially opening the interdigitating stiffening structure and at least partially unfolding at least one of the multiple longitudinally extending folds;
wherein a second longitudinal segment comprises a plurality of circumferentially spaced, arc-shaped, stiff wall portions as part of the outer tubular layer, the plurality of stiff wall portions extending parallel to and partially around the expandable inner layer; and
wherein the multiple longitudinally extending folds comprise a first longitudinally extending fold, a second longitudinally extending fold, and a third longitudinally extending fold equally spaced circumferentially around the expandable inner layer, the first and second longitudinally extending folds located radially inward of at least two stiff wall portions.

2. The sheath of claim 1, wherein the first longitudinal segment comprises an outermost cover as part of the outer tubular layer, the outermost cover configured to stretch to accommodate a passing implant.

3. The sheath of claim 1, wherein each of the stiff wall portions comprises a curved inner surface, a curved outer surface, a first straight edge extending between the curved inner and outer surfaces, and a straight second edge extending between the curved inner and outer surfaces, and wherein each curved outer surface of a selected stiff wall portion is wider than the corresponding curved inner surface of the selected stiff wall portion.

4. The sheath of claim 1, wherein the second longitudinal segment further comprises a plurality of longitudinally extending gaps between longitudinally extending edges of the stiff wall portions, and the second longitudinal segment of the sheath is configured to temporarily expand by widening the plurality of longitudinally extending gaps and unfolding at least one of the multiple longitudinally extending folds of the expandable inner layer to allow passage of an implant through the central lumen.

5. The sheath of claim 4, wherein a first longitudinally extending fold of the expandable inner layer is positioned between two circumferentially spaced stiff wall portions.

6. The sheath of claim 5, wherein when the sheath is in an unexpanded configuration, the first longitudinally extending fold is located radially inward of and is at least partially radially aligned with a first longitudinally extending gap.

7. The sheath of claim 5, wherein the first longitudinally extending fold is configured to at least partially unfold during expansion of the expandable inner layer, and wherein the at least partially unfolded portion of the first longitudinally extending fold is at least partially radially aligned with a first longitudinally extending gap.

8. The sheath of claim 1, wherein when the sheath is in an unexpanded configuration, overlapping portions of the multiple longitudinally extending folds extend along a length of the expandable inner layer, and the overlapping portions extend generally parallel to and partially around a central longitudinal axis of the sheath.

9. The sheath of claim 1, wherein the first and second longitudinally extending folds at least partially unfold during expansion of the expandable inner layer, the at least partially unfolded portion of the first longitudinally extending fold being at least partially radially aligned with a first longitudinally extending gap between two stiff wall portions, and the at least partially unfolded portion of the second longitudinally extending fold being at least partially radially aligned with a second longitudinally extending gap between two stiff wall portions.

10. The sheath of claim 1, wherein the at least two stiff wall portions include a first, second and third stiff wall portion each extending along a length of the second longitudinal segment, the first, second and third stiff wall portions oriented generally parallel to each other and extending in a direction generally parallel to a central longitudinal axis of the sheath, wherein the first, second, and third longitudinally extending folds each at least partially unfold during expansion of the inner member, and wherein the at least partially unfolded portions of the first, second, and third longitudinally extending folds are at least partially radially aligned with corresponding first, second and third longitudinally extending gaps between the first, second and third stiff wall portions.

11. A method of delivering an implant, the method comprising;
positioning a sheath within the vasculature of a subject,
advancing the implant into a lumen of the first longitudinal segment of the sheath,
exerting an outwardly directed radial force on the inner surface of a first longitudinal segment of the sheath via the implant,
at least partially unfolding at least one longitudinally extending fold of an inner expandable layer of the first longitudinal segment via the outwardly directed radial force,
at least partially opening an interdigitating stiffening structure of an outer tubular layer of the first longitudinal segment via the outwardly directed radial force,
advancing the implant into a lumen of the second longitudinal segment of the sheath,
exerting an outwardly directed radial force on the inner surface of the second longitudinal segment of the sheath via the implant,
at least partially unfolding at least one longitudinally extending fold of an inner expandable layer of the second longitudinal segment via the outwardly directed radial force,
widening a plurality of longitudinally extending gaps of the outer tubular layer of the second longitudinal segment via the outwardly applied radial force,
positioning the implant within the vasculature of the subject.

12. The method of claim 11, wherein the interdigitating stiffening structure surrounds the expandable inner layer and comprises a plurality of protrusions facing in alternating circumferential directions and interdigitating between each other.

13. The method of claim 12, wherein opening the interdigitating stiffening structure comprises sliding the interdigitating protrusions circumferentially with respect to each other.

14. The method of claim 13, wherein opening the interdigitating stiffening structure comprises sliding a plurality of ends of the protrusions circumferentially toward each other and then away from each other.

15. The method of claim 14, wherein opening the interdigitating stiffening structure comprises moving a plurality of ends of the protrusions away from each other so as to introduce an elongated space in the outer tubular layer.

16. The method of claim 11, wherein at least partially unfolding at least one longitudinally extending fold of an inner expandable layer of the first longitudinal segment via the outwardly directed radial force comprises at least partially unfolding three circumferentially spaced longitudinally extending folds of the inner expandable layer of the first longitudinal segment.

* * * * *